US 7,128,735 B2

(12) United States Patent
Weston

(10) Patent No.: US 7,128,735 B2
(45) Date of Patent: Oct. 31, 2006

(54) REDUCED PRESSURE WOUND TREATMENT APPLIANCE

(76) Inventor: Richard Scott Weston, 6965 El Camino real, #105 602, La Costa, CA (US) 92009

( * ) Notice: Subject to any disclaimer, the term of this patent is extended or adjusted under 35 U.S.C. 154(b) by 0 days.

(21) Appl. No.: 11/026,733

(22) Filed: Dec. 30, 2004

(65) Prior Publication Data

US 2005/0148913 A1 Jul. 7, 2005

Related U.S. Application Data

(60) Provisional application No. 60/533,967, filed on Jan. 2, 2004.

(51) Int. Cl.
*A61M 27/00* (2006.01)
*A61M 1/00* (2006.01)
*A61F 13/00* (2006.01)

(52) U.S. Cl. .................. 604/543; 604/313; 604/308; 604/540; 602/13

(58) Field of Classification Search ........ 604/313–316, 604/305, 540–544, 308; 602/13; 128/887
See application file for complete search history.

(56) References Cited

U.S. PATENT DOCUMENTS

| 1,585,104 | A | 5/1926 | Montgomery |
|---|---|---|---|
| 1,732,310 | A | 10/1929 | Naibert |
| 1,863,534 | A | 6/1932 | Odell |
| 1,936,129 | A | 11/1933 | Fisk |
| 2,318,888 | A | 5/1943 | Sanders |
| 2,366,799 | A | 1/1945 | Luisada |
| 2,385,683 | A | 9/1945 | Burton |
| 3,217,707 | A | 11/1965 | Werding |
| 3,238,937 | A | 3/1966 | Stein |
| 3,286,711 | A | 11/1966 | MacLeod |
| 3,315,665 | A | 4/1967 | MacLeod |
| 3,465,748 | A | 9/1969 | Kravchenko |
| 3,572,340 | A | * 3/1971 | Lloyd et al. ............... 604/133 |
| 3,712,298 | A | 1/1973 | Snowdon et al. |
| 3,794,035 | A | 2/1974 | Brenner |

(Continued)

FOREIGN PATENT DOCUMENTS

CA 2049978 C 10/1990

(Continued)

OTHER PUBLICATIONS

Chariker, M.E., et al, "Effective Management of Incisional and Cutaneous Fistulae with Closed Suction Wound Drainage," Contemporary Surgery. Jun. 1989, pp. 59-63, vol. 34 USA.

(Continued)

*Primary Examiner*—Tatyana Zalukaeva
*Assistant Examiner*—Laura C Hill
(74) *Attorney, Agent, or Firm*—Kenneth P. Krohn

(57) ABSTRACT

A wound treatment appliance is provided for treating a wound, which appliance comprises a semi-rigid or rigid wound covering device and a vacuum system to provide a supply of reduced pressure to the wound covering device. The wound covering device may be comprised of an impermeable overlay, a stopper, and a suction drain. Alternatively, the wound covering device may be comprised of an impermeable overlay and a suction drain. The wound covering device may also be comprised of an impermeable overlay that has at least one channel that is a part thereof, wherein the at least one channel is used to provide reduced pressure to the wound and may remove fluid aspirated from the wound. The vacuum system may be comprised of at least a vacuum pump or a suction bulb, or a combination of the same. Finally, methods for using the wound treatment appliance are provided.

82 Claims, 7 Drawing Sheets

U.S. PATENT DOCUMENTS

| | | | |
|---|---|---|---|
| 3,859,989 A | | 1/1975 | Spielberg |
| 3,908,642 A | | 9/1975 | Vinmont |
| 3,961,625 A | | 6/1976 | Dillon |
| 3,988,793 A | | 11/1976 | Abitbol |
| 4,421,109 A | | 12/1983 | Thornton |
| 4,432,354 A | | 2/1984 | Lasley |
| 4,738,249 A | | 4/1988 | Linman et al. |
| 4,950,483 A | | 8/1990 | Ksander et al. |
| 4,969,880 A | * | 11/1990 | Zamierowski ............ 604/305 |
| 5,000,164 A | | 3/1991 | Cooper |
| 5,228,431 A | | 7/1993 | Giarretto |
| 5,243,968 A | | 9/1993 | Byun |
| 5,307,791 A | | 5/1994 | Senoue et al. |
| 5,425,742 A | | 6/1995 | Joy |
| 5,462,514 A | | 10/1995 | Harris |
| 5,549,584 A | * | 8/1996 | Gross ........................ 604/313 |
| 5,577,994 A | | 11/1996 | Celik |
| 5,636,643 A | * | 6/1997 | Argenta et al. ............ 128/897 |
| 5,645,981 A | | 7/1997 | Romanet et al. |
| 5,688,225 A | | 11/1997 | Walker |
| 5,701,917 A | | 12/1997 | Khouri |
| 5,827,246 A | | 10/1998 | Bowen |
| 5,893,368 A | | 4/1999 | Sugerman |
| 5,938,626 A | | 8/1999 | Sugerman |
| 6,045,541 A | | 4/2000 | Matsumoto et al. |
| 6,135,166 A | | 10/2000 | Paradies et al. |
| D434,150 S | | 11/2000 | Tumey et al. |
| 6,142,982 A | | 11/2000 | Hunt et al. |
| 6,458,109 B1 | * | 10/2002 | Henley et al. ............ 604/304 |
| 6,595,949 B1 | | 7/2003 | Shapiro |
| 2002/0065494 A1 | * | 5/2002 | Lockwood et al. ........ 604/313 |
| 2002/0068913 A1 | | 6/2002 | Fleischmann |
| 2002/0115952 A1 | | 8/2002 | Johnson |
| 2002/0143286 A1 | | 10/2002 | Tumey |
| 2002/0161346 A1 | | 10/2002 | Lockwood et al. |
| 2002/0183702 A1 | | 12/2002 | Henley et al. |
| 2002/0198503 A1 | | 12/2002 | Risk |
| 2002/0198504 A1 | | 12/2002 | Risk |
| 2003/0040687 A1 | | 2/2003 | Boynton et al. |
| 2003/0050594 A1 | | 3/2003 | Zamierowski |
| 2003/0125646 A1 | | 7/2003 | Whitlock |
| 2004/0073151 A1 | * | 4/2004 | Weston ........................ 602/41 |
| 2005/0148913 A1 | | 7/2005 | Weston |
| 2005/0203452 A1 | | 9/2005 | Weston et al. |

FOREIGN PATENT DOCUMENTS

| | | |
|---|---|---|
| CA | 2369000 A1 | 10/1990 |
| CA | 2103033 C | 11/1992 |
| CA | 2414393 A1 | 11/1992 |
| CA | 2121688 C | 5/1993 |
| CA | 2115951 A1 | 8/1994 |
| CA | 2157772 C | 9/1994 |
| CA | 2198243 A1 | 2/1996 |
| CA | 2216791 C | 10/1996 |
| CA | 2237606 A1 | 5/1997 |
| CA | 2238413 A1 | 5/1997 |
| CA | 2267312 A1 | 4/1998 |
| CA | 2272372 A1 | 5/1998 |
| CA | 2285470 A1 | 9/1998 |
| CA | 2303085 A1 | 3/1999 |
| CA | 2471780 A1 | 3/1999 |
| CA | 2347115 A1 | 4/2000 |
| CA | 2367460 A1 | 10/2000 |
| CA | 2369022 C | 10/2000 |
| CA | 2369024 A1 | 10/2000 |
| CA | 2368085 A1 | 11/2000 |
| CA | 2390513 A1 | 5/2001 |
| CA | 2408305 A1 | 11/2001 |
| CA | 2458285 A1 | 3/2003 |
| CA | 2483654 A1 | 11/2003 |
| CA | 2490027 A1 | 12/2003 |
| CA | 2486274 A1 | 9/2004 |

OTHER PUBLICATIONS

Biblehimer, Helen L., "Dealing With a Wound that Drains 1.5 Liters a Day," RN, Aug. 1986, pp. 21-23, USA.

Wooding-Scott, Margaret, et.al, "No Wound is Too Big for Resourceful Nurses," RN, Dec. 1988, pp. 22-25, USA.

Garcia-Renaldi, Raul, et al, "Improving the Eficiency of Wound Drainage Catheters, " Journal of Surgery (?), Sep. 1975, pp. 372-373, vol. 130.

Schwab, Peter M. and Kelly, Keith A., "Primary closure of the Perineal Wound After Proctectomy,"Mayo Clinic Proc., Mar. 1974, pp. 176-179, vol. 49, USA.

Ramirez, Oscar M., et al, "Optimal Wound Healing Under Op-Site Dressing," pp. 474-475, vol. 73, No. 3.

Raffl, Arthur B., "Use of Negative Pressure Under Skin Flaps After Radical Mastectomy, "Dept. of Surgery, State Univ. of N.Y., College of Medicine, Syracuse, NY, Submitted for publication Apr. 1953, p. 1048, USA.

Knight, Marie Ray, A Second Skin for Patients with Large Draining Wounds, Nursing, Jan. 1976, p. 37, USA.

Finley, John M., "Practical Wound Management," pp. 45, 127, 143, 149, 207.

Spengler, Michael D., et al, "Performance of Filtered Sump Wound Drainage Tubes", Surgery, Gynecology & Obstetrics, Mar. 1982, pp. 333-336, vol. 54, USA.

Kohlman, Phyllis A., et al, "Pouching Procedure to Collect Drainage From Around a Biliary Drainage Catheter," Ostomy/Wound Management, Nov./Dec. 1991, pp. 47-50, vol. 37.

Alper, Joseph, C., "Recent Advances in Moist Wound Healing," Southern Medical Journal, Nov. 1988, pp. 1398-1404, vol. 79, No. 11 USA.

Reid, Daniel P., "Information on Cupping or using suction Cups on Wounds and for healing purposes", From Chinese Herbal Medicine.

Taylor, Virginia, Meeting the Challenge oF Fistulas & Draining Wounds, Nursing, Jun. 1980, pp. 45-51, USA.

"General Characteristics of Wound Healing and Russian Classification of Wound Healing Process".

Davydov, Yu. A., et al, Article in Russian (?): Abstract in English: "Vacuum Therapy in the Treatment of Purulent Lactation Mastitis", pp. 66-70.

Davydov, Yu. A., et al, Article in Russian (?): Abstract in English: "The Bacteriological and Cytological Assessment of Vacuum Therapy of Purulent Wounds", pp. 48-52.

Article 3, Article in Russian (?), 1991, pp. 126-128.

Article 4, Article in Russian (/), 1991, pp. 132-135.

Alexander, J. Wesley, "Prevention of Wound Infections," The American Journal of Surgery, Jul. 1976, pp. 59-63, vol. 132, USA.

Sheppard, M.D., "Sealed Drainage of Wounds", The Lancet, Jun. 14, 1952, pp. 1174-1176.

Putney F. Johnson, "The Use of Continuous Negative Pressure after Laryngectomy and Radical Neck Dissection", Surgery, Gynecology & Obstetrics, Aug. 1956, pp. 244-246, USA.

Brummelkamp, W.H., et al, "High-vacuum drainage and primary perineal wound closure in abdominoperineal excision of the rectum", The Netherlands Journal of Surgery, 1991 pp. 236-238, Netherlands.

Miles, W. Ernest, "Technique of the Radical Operation for Cancer of the Rectum", The British Journal of Surgery, pp. 292-304, United Kingdom.

UNKNOWN, "Wound Suction", Nursing, Oct. 1975, pp. 52-53, USA.

Brubacker, Lynda L., "To Heal A Draining Wound", RN, Mar. 1982, pp. 30-35, USA.

Betancourt, Sergio, "A Method of Collecting the Effluent from Complicated Fistual of the Small Intestine," Dept. of Surgery, Allegheny General Hospital, Pittsburgh, p. 375, USA.

Wolthius, Roger A., et al, "Physiological Effects of Locally Applied Reduced Pressure in Man," Physiological Reviews, Jul. 1974, pp. 566-595 vol. 54, No. 3, USA.

Zamierowski, David S., Letter: "All Foam Sponges are not Equal in Vacuum Dressings," British Journal of Plastic Surgery, 1999, 52, 78-81, p. 79, United Kingdom.

Spahn, Slide presented at the WOCN meeting in Ontario, California, Sep. 2001.

UNKNOWN, "The RN Magazine/University of California Continuing Education Curriculum; Examination on 'To heal a draining wound'", RN, Mar. 1982, p. 36, USA.

UNKNOWN, Medela product information in English Summary: "Pieupump MK II is the new micro-data controlled thoracic drainage".

Larichev, A. B., Vacuum Therapy of Wounds and Wound Infection, 2005 (BlueSky Publishing, Carlsbad, California), all pages.

The Kremlin Papers, Perspectives in Wound Care, 2004 (Blue Sky Publishing, Carlsbad, California), all pages.

\* cited by examiner

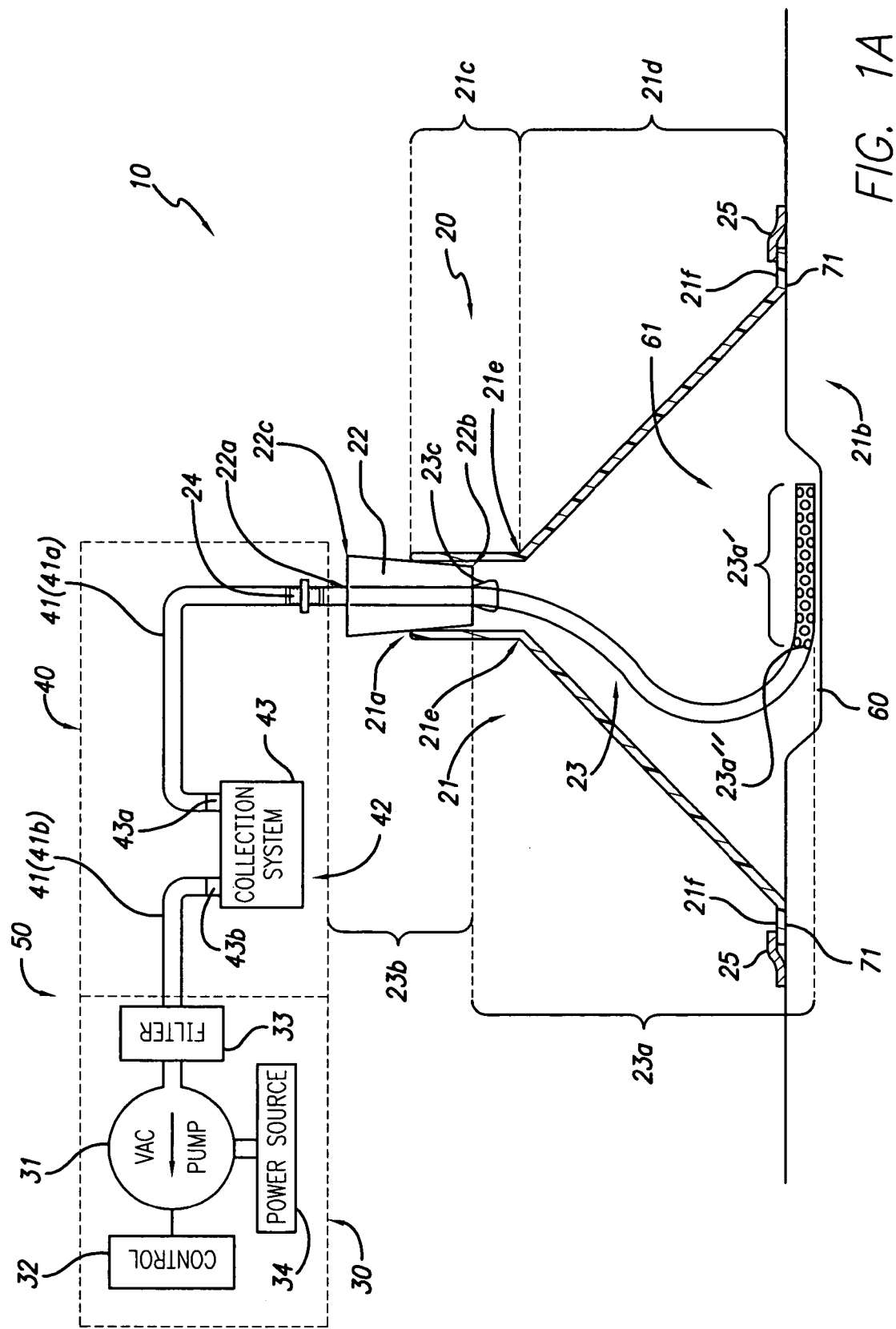

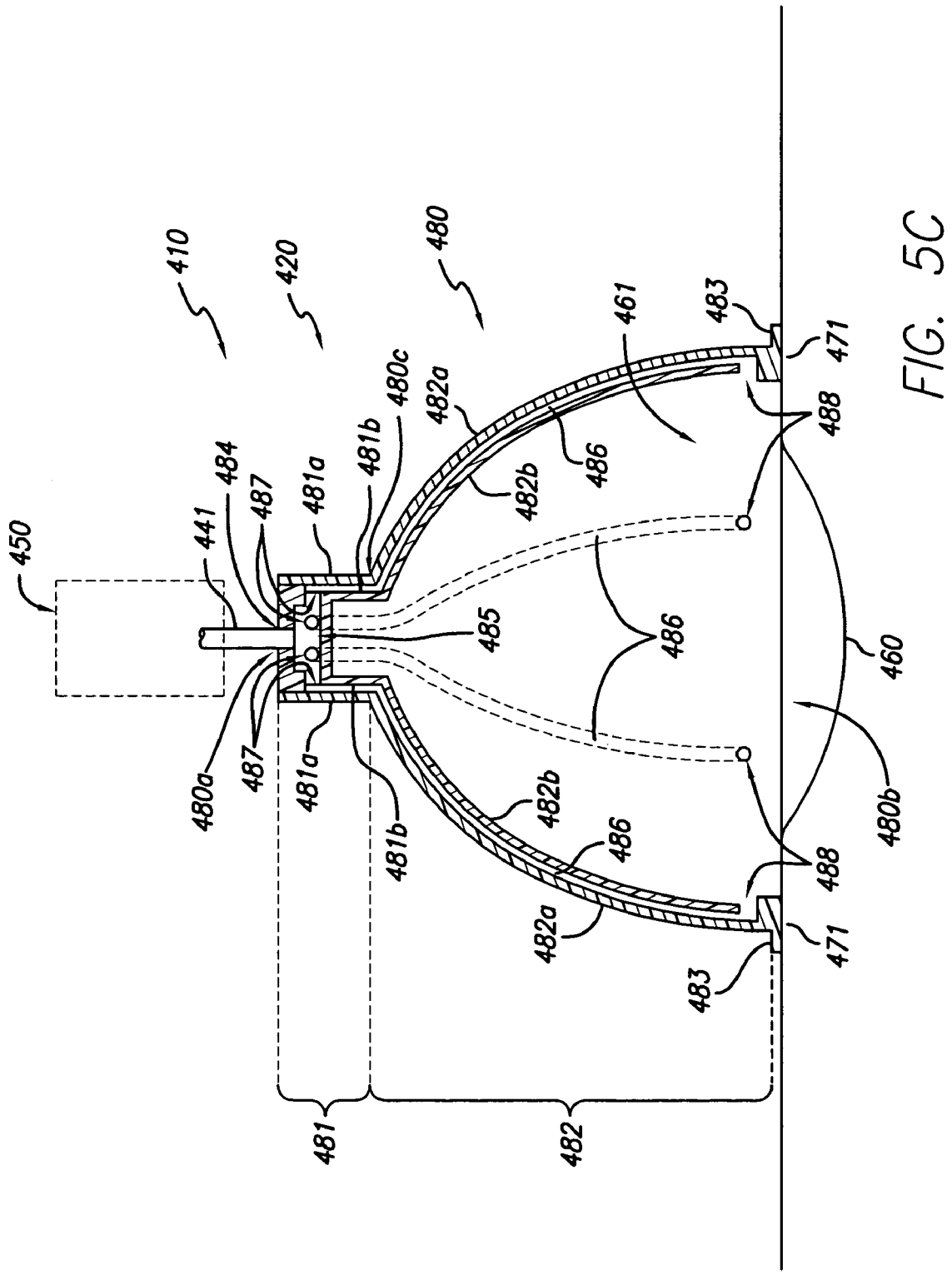

REDUCED PRESSURE WOUND TREATMENT APPLIANCE

CROSS REFERENCES TO OTHER APPLICATIONS

This application claims the benefit of U.S. provisional application No. 60/533,967, filed on Jan. 2, 2004. The full disclosure of this provisional application is incorporated herein by reference.

BACKGROUND

The present invention generally relates to treatment of wounds, and more specifically to an improved apparatus and methods for treating all or a portion of a wound by applying reduced pressure to the portion of the wound for which treatment is desired. In this context, the term "wound" is to be interpreted broadly, to include any body part of a patient that may be treated using reduced pressure.

The treatment of open or chronic wounds that are too large to spontaneously close or otherwise fail to heal by means of applying reduced pressure to the site of the wound is well known in the art. One such system is disclosed in U.S. patent application Ser. No. 10/652,100), which was filed by the present inventor with the U.S. Patent and Trademark Office on Aug. 28, 2003. The disclosure of this U.S. patent application is incorporated herein by reference. Another system is disclosed in U.S. patent application Ser. No. 11/064,813, entitled "Improved Flexible Reduced Pressure Treatment Appliance," which was filed by the present inventor on Feb. 24, 2005. The disclosure of this U.S. patent application is also incorporated herein by reference.

Reduced pressure wound treatment systems currently known in the art commonly involve placing a cover that is impermeable to liquids over the wound, using various means to seal the cover to the tissue of the patient surrounding the wound, and connecting a source of reduced pressure (such as a vacuum pump) to the cover in a manner so that an area of reduced pressure is created under the cover in the area of the wound. However, rigid and semi-rigid covers currently known and used in the relevant art for this purpose have a number of disadvantages. For example, such covers typically do not include a means to cleanse and provide other treatment to the wound without removing the cover from the tissue surrounding the wound. Thus, cleansing and other treatment of the wound may necessitate more frequent cover changes. This additional step of removing the cover, cleansing or otherwise treating the wound, and then replacing the cover, also generally increases the time medical staff must expend in treating the wound. This additional time generally means additional expense incurred in cleansing or other treatment of the wound. Further, the additional required changes of the cover for this purpose may also cause pain or discomfort or both for the patient. Further, the additional changes of the cover for this purpose may present an increased risk of infection or contamination of the wound.

Therefore, there is a need for a rigid or semi-rigid reduced pressure wound treatment system that has an enclosing means to enclose a wound and yet provide for cleansing and other treatment of the wound without the need to replace the enclosing means. Such enclosing means would simplify cleansing and other treatment of the wound. It would also generally save the valuable time of medical staff. As a result, it would also generally reduce the expense involved in wound treatment. It would also tend to reduce patient pain and discomfort and reduce the risk of wound infection and contamination. There is also a need for an enclosing means that is relatively inexpensive, while meeting the needs described above.

Finally, there is a need for a semi-rigid or rigid enclosing means that has within it a means to provide reduced pressure to the area of the wound under the enclosing means so that fluid aspirated from the wound is drawn through channels in the enclosing means. This type of enclosing means would potentially be easier to construct. Thus, it may also be less expensive to manufacture. In addition, this enclosing means may be made from materials that would allow it to be reusable. It would also provide for therapy that may occur as a patient sleeps, as described in more detail below.

SUMMARY

The present invention is directed to a reduced pressure wound treatment appliance and methods that satisfy the needs described above. As described in greater detail below, they have many advantages over existing reduced pressure wound treatment apparatus and methods when used for their intended purpose, as well as novel features that result in a new reduced pressure wound treatment appliance and methods that are not anticipated, rendered obvious, suggested, or even implied by any of the prior art apparatus or methods, either alone or in any combination thereof.

In accordance with the present invention, a wound treatment appliance is provided for treating all or a portion of a wound by applying reduced pressure (i.e., pressure that is below ambient atmospheric pressure) to the portion of the wound to be treated in a controlled manner for a selected time period in a manner that overcomes the disadvantages of currently existing apparatus. The application of reduced pressure to a wound provides such benefits as faster healing, increased formation of granulation tissue, closure of chronic open wounds, reduction of bacterial density within wounds, inhibition of burn penetration, and enhancement of flap and graft attachment. Wounds that have exhibited positive response to treatment by the application of negative pressure include infected open wounds, decubitus ulcers, dehisced incisions, partial thickness burns, and various lesions to which flaps or grafts have been attached.

A first version of the appliance is comprised of an impermeable overlay, a stopper, a suction drain, suction drain sealing means (which are discussed in more detail below), and reduced pressure supply means (which are also discussed in more detail below). In the embodiments of this first version of the invention, the impermeable overlay is comprised of a top end having an opening therein and a bottom end having an opening therein. The bottom end is positioned over the wound on the tissue surrounding the wound so that the impermeable overlay encloses the wound and forms an approximately hermetic seal with such tissue. In addition, the impermeable overlay is sufficiently rigid so that it supports the stopper and is supported out of contact from the wound. The stopper has a port therein and is removably positioned in the top end opening of the impermeable overlay, forming an approximately hermetic seal with the top end opening of the impermeable overlay. The suction drain is further comprised of a top drain portion positioned within the port in the stopper and a bottom drain portion extending from the top drain portion into the area of the wound under the impermeable overlay. The suction drain sealing means, which is described in more detail below, is used to seal the top drain portion to the port in the stopper. The reduced pressure supply means, which is described in more detail below, is used to connect the top portion of the suction drain to a reduced pressure supply source that provides a supply of reduced pressure to the suction drain, so that the area under the impermeable overlay in the area of the wound is supplied with reduced pressure by the reduced pressure supply source.

In some embodiments of this first version of the invention, the impermeable overlay is approximately bell-shaped, the bottom end opening of the impermeable overlay having a larger diameter than the top end opening of the impermeable overlay. In other embodiments, the impermeable overlay may be comprised of an overlay top portion and an overlay bottom portion, wherein the overlay bottom portion is approximately conical in shape, having a larger opening at one end and a smaller opening at the other end, the larger opening being the bottom end opening of the impermeable overlay. The overlay top portion is approximately in the shape of a cylindrical tube having an opening at each end, one opening being the top end opening of the impermeable overlay and the other opening being adjacent to the smaller opening of the overlay bottom portion. In some of these embodiments, the overlay bottom portion may further comprise a flange portion that is adjacent to and extends around the perimeter of the exterior portion of the bottom open end of the impermeable overlay. The overlay bottom portion may also further comprise padding material that is placed between the perimeter of the bottom end opening and the tissue surrounding the wound. In still other embodiments, the impermeable overlay may be comprised of an approximately conically-shaped semi-rigid flange portion adjacent to the perimeter of the bottom end opening, an approximately conically-shaped flexible center portion that extends away from the semi-rigid flange portion, a cylindrical tubular overlay top portion extending away from the flexible center portion, wherein the distal open end of the overlay top portion is the top end opening of the impermeable overlay and the overlay top portion is sufficiently rigid to hold and support the stopper, and at least two support members that are each connected at one end to the semi-rigid flange portion and at the other end to the overlay top portion, the at least two support members being sufficiently rigid to support the overlay top portion out of contact with the semi-rigid flange portion. In yet other embodiments of this first version of the invention, the top end opening of the impermeable overlay is approximately in the shape of a circle, the stopper is approximately in the shape of a cylinder being tapered along its longitudinal axis so that one base of the cylinder has a smaller diameter than the other base, and the smaller diameter base of the stopper is within the volume of the impermeable overlay and the larger diameter base of the stopper is outside the volume of the impermeable overlay when the stopper is removably positioned in the top end opening of the impermeable overlay.

In some embodiments of this first version of the invention, the port in the stopper is approximately cylindrical in shape and the suction drain is approximately tubular in shape. In some of these embodiments, the top drain portion and the bottom drain portion of the suction drain are comprised of flexible tubing. In yet other embodiments, the bottom drain portion of the suction drain is further comprised of wound suction means that may be used to remove debris, exudate and other matter from the wound. In some of these embodiments, the wound suction means may be comprised of a wound suction member and wound suction member attachment means (which are described in more detail below) to connect the wound suction member to the bottom drain portion in a manner so that the bottom drain portion is in fluid communication with the wound suction member. In some of these embodiments, the wound suction member may have an approximately rectangular cross section, a hollow interior, and at least one perforation in the surface of the wound suction member. In yet other embodiments, the top drain portion of the suction drain is further comprised of tubing connection means, which are described in more detail below, that are used to removably connect the reduced pressure supply means to the top drain portion of the suction drain.

In yet other embodiments of this first version of the invention, the appliance further comprises a reduced pressure supply source that at least produces a supply of reduced pressure. In these embodiments, the reduced pressure supply source is connected to the top portion of the suction drain by the reduced pressure supply means, so that the area under the impermeable overlay in the area of the wound is supplied with reduced pressure by the reduced pressure supply source. In some of these embodiments, the reduced pressure supply source may be comprised of a suction bulb having an inlet port and an outlet port, an exhaust tubing member operably connected to the outlet port, and an exhaust control valve operably connected to the exhaust tubing member. The inlet port is connected to the reduced pressure supply means and fluids generally exit the suction bulb by means of the outlet port. Also in some of these embodiments, the reduced pressure supply source is further comprised of a filter operably positioned in the exhaust tubing member, wherein the filter prevents the venting of micro-organisms aspirated from the wound. In some of these embodiments, the filter may also be a hydrophobic filter that prevents the venting of fluids aspirated from the wound. In yet other embodiments, the reduced pressure supply source may be comprised of a vacuum pump, which may be a portable vacuum pump in some embodiments. In some embodiments, the reduced pressure supply source may further comprise a control system for the vacuum pump, wherein the control system controls at least the level of suction produced by the vacuum pump or the rate of fluid flow produced by the vacuum pump or any combination of rate of suction and rate of fluid flow of the vacuum pump. Also in some of these embodiments, the reduced pressure supply source further comprises a filter operably positioned between the vacuum pump and the reduced pressure supply means, wherein the filter prevents the venting of and contamination of the vacuum pump by micro-organisms aspirated from the wound. In some of these embodiments, the filter may also be a hydrophobic filter that also prevents the venting of and contamination of the vacuum pump by fluids aspirated from the wound. In some embodiments of this first version of the invention, the reduced pressure supply means is comprised of flexible tubing. In other embodiments, the reduced pressure supply means may be further comprised of a collection system that is operably positioned between the stopper and the reduced pressure supply source. In some of these embodiments, the collection system may comprise a container to receive and hold fluid aspirated from the wound. Further, in some of these embodiments, the reduced pressure supply means may be further comprised of flexible tubing that connects the collection system to the suction drain and the collection system to the reduced pressure supply source. Also in some of these embodiments, the collection system may be further comprised of pressure halting means to halt the application of reduced pressure to the wound when the fluid in the container exceeds a predetermined amount. In some of these embodiments, the reduced pressure supply means may be further comprised of a tubing member that is connected to the collection system and the pressure halting means is comprised of a flotation valve within the container for blocking the flexible tubing member when a predetermined amount of fluid is collected within the container. In some embodiments of this first version of the invention, the reduced pressure under the impermeable overlay in the area of the wound is in the range from approximately 20 mm of Hg below atmospheric pressure to approximately 125 mm of Hg below atmospheric pressure. In other embodiments, the reduced pressure may be applied in a cyclic nature, the cyclic nature providing alternating time periods of application of reduced pressure and without application of reduced pressure.

Another embodiment of this first version of the invention includes a method of using the appliance to treat a wound, which comprises the following steps. First, the suction drain is operably positioned in the port in the stopper. Second, the stopper is operably positioned in the top end opening of the impermeable overlay. Third, the bottom end of the impermeable overlay is operably placed over the wound. Fourth, the suction drain is operably connected to the reduced pressure supply source using the reduced pressure supply means. It should be noted that the preceding steps may generally be performed in any order. Fifth, the reduced pressure supply source is operated in a manner so that it provides a supply of reduced pressure to maintain reduced pressure in the area of the wound under the impermeable overlay. Sixth, reduced pressure is maintained in the area of the wound under the impermeable overlay until the wound being treated has progressed toward a selected stage of healing. In other embodiments, this method may further comprise the step of removing the stopper from the top end opening of the impermeable overlay to provide access for treatment of the wound. In yet other embodiments, this method may further comprise the step of manipulating the suction drain so that the suction drain removes debris, fluid and other material from the area of the wound under the impermeable overlay. In still other embodiments, the reduced pressure is from about 20 mm of Hg below atmospheric pressure to about 125 mm of Hg below atmospheric pressure. In other embodiments, the reduced pressure is applied in a cyclic nature, the cyclic nature providing alternating time periods of application of reduced pressure and without application of reduced pressure. In some of these embodiments, the pressure may be applied for a period of approximately 6 to 8 hours during a period each day when the patient is sleeping.

In yet other embodiments of this first version of the invention, the appliance may comprise a wound covering device and a vacuum system. In these embodiments, the wound covering device is further comprised of an impermeable overlay, tissue sealing means (which are described in more detail below), a stopper, a suction drain, and suction drain sealing means (which are discussed in more detail below). In these embodiments, the impermeable overlay is comprised of a top end having an opening therein and a bottom end having an opening therein. The bottom end is positioned over the wound on the tissue surrounding the wound so that the impermeable overlay encloses the wound. The impermeable overlay is also sufficiently rigid to be supported out of contact with the wound. The tissue sealing means, which is described in more detail below, is used to seal the impermeable overlay to tissue surrounding the wound so that the impermeable overlay is adapted to maintain reduced pressure under the impermeable cover in the area of the wound. In these embodiments, the stopper has a port and is removably positioned in the top end opening of the impermeable overlay, forming an approximately hermetic seal with the top end opening of the impermeable overlay. Also in these embodiments, the suction drain is comprised of a top drain portion positioned within the port in the stopper and a bottom drain portion extending from the top drain portion into the area of the wound under the impermeable overlay. The top drain portion forms an approximately hermetic seal with the port using the suction drain sealing means. In these embodiments, the vacuum system is comprised of a reduced pressure supply source for at least providing a supply of reduced pressure, reduced pressure supply means, and a collection system. In various embodiments, the reduced pressure supply source may be comprised of at least a suction bulb, a vacuum pump, or a portable vacuum pump, or any combination thereof. The reduced pressure supply means, which are described in more detail below, are used to connect the reduced pressure supply source to the wound covering device, so that the area under the wound covering device in the area of the wound is supplied with reduced pressure by the reduced pressure supply source. The collection system is operably positioned within the reduced pressure supply means between the wound covering device and the reduced pressure supply source. The collection system also comprises a container to receive and hold fluid aspirated from the wound. In some embodiments, the vacuum system may also comprise a filter, which may be operably positioned between the reduced pressure supply source and the reduced pressure supply means to prevent the venting of or contamination of the reduced pressure supply source by (or both) micro-organisms or fluid aspirated from the wound (or both). In various embodiments of this first version of the invention, the impermeable overlay, the stopper, the suction drain, and suction drain sealing means of the wound covering device may have substantially the same structure, features and characteristics of the impermeable overlays, the stoppers, the suction drains, and suction drain sealing means described above in relation to this first version of the invention. Also, in some of these embodiments, the tissue sealing means may be the reduced pressure maintained under the wound covering device. In other embodiments, the tissue sealing means may be an adhesive tape, which may also be used to hold the impermeable overlay in place in the event of loss of reduced pressure in the area under the impermeable overlay. In yet other embodiments, the tissue sealing means may be a stretch fabric that covers the wound covering device and is wrapped around a portion of the body of the patient in the area of the wound.

A second version of the appliance is comprised of an impermeable overlay, a suction drain, suction drain sealing means (which are discussed in more detail below), and reduced pressure supply means (which are also discussed in more detail below). In the embodiments of this second version of the invention, the impermeable overlay is comprised of a port end having a port therein and a bottom end having an opening therein. The bottom end is positioned over the wound on the tissue surrounding the wound so that the impermeable overlay encloses the wound and forms an approximately hermetic seal with such tissue. In addition, the impermeable overlay is sufficiently rigid so that it is supported out of contact from the wound. The suction drain is further comprised of a top drain portion positioned within the port in the port end and a bottom drain portion extending from the top drain portion into the area of the wound under the impermeable overlay. The suction drain sealing means, which is described in more detail below, is used to seal the top drain portion to the port in the port end. The reduced pressure supply means, which is described in more detail below, is used to connect the top portion of the suction drain to a reduced pressure supply source that provides a supply of reduced pressure to the suction drain, so that the area under the impermeable overlay in the area of the wound is supplied with reduced pressure by the reduced pressure supply source. In the various embodiments of this second version of the invention, the impermeable overlay may have substantially the same structure, features and characteristics as the impermeable overlay of the first version of the invention described above, except that the port end in this second version is substituted for the open end of the impermeable overlay of the first version, and the port in the port end has substantially the same structure, features and characteristics as the port in the stopper in the first version of the invention described above. Also, the suction drain, the suction drain sealing means, and the reduced pressure supply means of this second version of the invention may have substantially the same structure, features and characteristics as the suction drain, the suction drain sealing means, and the reduced pressure supply means, respectively, of the first version of the invention described above, except that the suction drain sealing means is used to seal the top drain portion of the suction drain to the port in the port end in this second version.

In yet other embodiments of this second version of the invention, the appliance further comprises a reduced pressure supply source that produces a supply of reduced pressure. In these embodiments, the reduced pressure supply source is connected to the top portion of the suction drain by the reduced pressure supply means, so that the area under the impermeable overlay in the area of the wound is supplied with reduced pressure by the reduced pressure supply source. In all of these embodiments, the reduced pressure supply source and the reduced pressure supply means of this second version of the invention may have substantially the same structure, features and characteristics as the reduced pressure supply source and the reduced pressure supply means, respectively, of the first version of the invention described above. In some embodiments of this second version of the invention, the reduced pressure under the impermeable overlay in the area of the wound is in the range from approximately 20 mm of Hg below atmospheric pressure to approximately 125 mm of Hg below atmospheric pressure. In other embodiments, the reduced pressure may be applied in a cyclic nature, the cyclic nature providing alternating time periods of application of reduced pressure and without application of reduced pressure.

Another embodiment of this second version of the invention includes a method of using the appliance of the second version to treat a wound, which comprises the following steps. First, the suction drain is operably positioned in the port in the port end. Second, the bottom end of the impermeable overlay is operably placed over the wound. Third, the suction drain is operably connected to the reduced pressure supply source using the reduced pressure supply means. It should be noted that the preceding steps may generally be performed in any order. Fourth, the reduced pressure supply source is operated in a manner so that it provides a supply of reduced pressure to maintain reduced pressure in the area of the wound under the impermeable overlay. Fifth, reduced pressure is maintained in the area of the wound under the impermeable overlay until the wound being treated has progressed toward a selected stage of healing. In other embodiments, this method may further comprise the step of manipulating the suction drain so that the suction drain removes debris, fluid and other material from the area of the wound under the impermeable overlay.

In still other embodiments, the reduced pressure is from about 20 mm of Hg below atmospheric pressure to about 125 mm of Hg below atmospheric pressure. In other embodiments, the reduced pressure is applied in a cyclic nature, the cyclic nature providing alternating time periods of application of reduced pressure and without application of reduced pressure. In some of these embodiments, the pressure may be applied for a period of approximately 6 to 8 hours during a period each day when the patient is sleeping.

Thus, it can be observed that in operating the appliance of the first and second versions of the present invention, the user of the appliance may remove the stopper in some embodiments in order to gain access to the area of the wound under the impermeable overlay to provide additional treatment, such as irrigation of the wound. This access is provided without the need to remove the impermeable overlay from the tissue surrounding the wound. In addition, the user may move the bottom drain portion of the suction drain in the area of the wound without removing the impermeable overlay. The appliance therefore provides the user with the ability to remove debris, fluids and other material from the area of the wound without removing the impermeable overlay.

A third version of the appliance is comprised of an impermeable overlay and reduced pressure supply means, which are discussed in more detail below. In the embodiments of this third version of the invention, the impermeable overlay is comprised of a port end having a port therein, a bottom end having an opening therein, and at least one channel. The bottom end is positioned over the wound on the tissue surrounding the wound so that the impermeable overlay encloses the wound and forms an approximately hermetic seal with such tissue. In addition, the impermeable overlay is sufficiently rigid so that it is supported out of contact from the wound. The at least one channel is in fluid communication with the port at the port end and extends from the port approximately parallel to a surface of the impermeable overlay to a point between the port and the bottom open end, where it terminates at an opening in the interior surface of the impermeable overlay so that the area of the wound under the impermeable overlay is in fluid communication with the port. The reduced pressure supply means, which are described in more detail below, are used to connect the top portion of the port to a reduced pressure supply source that provides a supply of reduced pressure to the port, so that the area under the impermeable overlay in the area of the wound is supplied with reduced pressure by the reduced pressure supply source. In various embodiments of this third version of the invention, the impermeable overlay may have substantially the same structure, features and characteristics as the impermeable overlay of the second version of the invention described above, except that in this third version the at least one channel is present in the impermeable overlay and is in fluid communication with the port at one end of the at least one channel and is in fluid communication with the corresponding interior surface opening in the impermeable overlay at the other end of the at least one channel. In some embodiments of this third version of the invention, the at least one channel extends at least to within ¼ inch of the bottom end opening of the impermeable overlay. In other embodiments, there are at least two channels and the at least two channels terminate at openings that are different distances from the bottom open end of the impermeable overlay. In still other embodiments, there are four channels. In yet other embodiments of this third version of the invention, the appliance further comprises a reduced pressure supply source that produces a supply of reduced pressure. In these embodiments, the reduced pressure supply source is connected to the port in the port end by the reduced pressure supply means, so that the area under the impermeable overlay in the area of the wound is supplied with reduced pressure by the reduced pressure supply source. In all of these embodiments, the reduced pressure supply source and the reduced pressure supply means of this second version of the invention may have the same structure, features and characteristics as the reduced pressure supply source and the reduced pressure supply means, respectively, of the first version of the invention described above, except that the reduced pressure supply means connects the reduced pressure supply source to the port, rather than the suction tube of the first version of the invention. In some embodiments of this third version of the invention, the reduced pressure under the impermeable overlay in the area of the wound is in the range from approximately 20 mm of Hg below atmospheric pressure to approximately 125 mm of Hg below atmospheric pressure. In other embodiments, the reduced pressure may be applied in a cyclic nature, the cyclic nature providing alternating time periods of application of reduced pressure and without application of reduced pressure.

Another embodiment of this third version of the invention includes a method of using the appliance of the third version to treat a wound, which comprises the following steps. First, the bottom end of the impermeable overlay is operably placed over the wound. Second, the port in the port end is operably connected to the reduced pressure supply source using the reduced pressure supply means. It should be noted that the preceding steps may generally be performed in any order. Third, the reduced pressure supply source is operated in a manner so that it provides a supply of reduced pressure to maintain reduced pressure in the area of the wound under the impermeable overlay. Fourth, reduced pressure is maintained in the area of the wound under the impermeable overlay until the wound being treated has progressed toward a selected stage of healing. In still other embodiments, the reduced pressure is from about 20 mm of Hg below atmospheric pressure to about 125 mm of Hg below atmospheric pressure. In other embodiments, the reduced pressure is applied in a cyclic nature, the cyclic nature providing alternating time periods of application of reduced pressure and without application of reduced pressure. In some of these embodiments, the pressure may be applied for a period of approximately 6 to 8 hours during a period each day when the patient is sleeping.

The present invention therefore meets the needs discussed above in the Background section. For example, the rigid or semi-rigid reduced pressure wound treatment system has an enclosing means to enclose a wound and yet provide for cleansing and other treatment of the wound without the need to replace the enclosing means. Such enclosing means may simplify cleansing and other treatment of the wound. It may also generally save the valuable time of medical staff. As a result, it may also generally reduce the expense involved in wound treatment. It may also tend to reduce patient pain and discomfort and reduce the risk of wound infection and contamination. It is also relatively inexpensive, while meeting the needs described above. In addition, this enclosing means may be made from materials that would allow it to be reusable. It would also provide for therapy that may occur as a patient sleeps, as described in more detail herein.

There has thus been outlined, rather broadly, the more primary features of the present invention. There are additional features that are also included in the various embodiments of the invention that are described hereinafter and that form the subject matter of the claims appended hereto. In this respect, it is to be understood that the invention is not limited in its application to the details of construction and to the arrangements of the components set forth in the following description or illustrated in the following drawings. This invention may be embodied in the form illustrated in the accompanying drawings, but the drawings are illustrative only and changes may be made in the specific construction illustrated and described within the scope of the appended claims. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

The foregoing summary, as well as the following detailed description of the preferred embodiments of the present invention, will be better understood when read in conjunction with the appended drawings, in which:

FIG. 1A is a view of an embodiment of a wound treatment appliance of a first version of the present invention, in which an embodiment of a wound covering device is shown in cross-sectional elevational view from the side of the device as it covers a wound, and in which an embodiment of a vacuum system, depicted generally and shown in schematic elevation view, provides reduced pressure within the area under the wound covering device;

FIG. 5C is a cross-sectional elevational view of the embodiment of the wound covering device of FIG. 5A and FIG. 5B from the side of the wound covering device as it covers a wound and as taken along the lines 5C—5C of FIG. 5B, such embodiment illustrating another embodiment of a vacuum system, which is depicted generally and shown in schematic elevation view.

DETAILED DESCRIPTION OF THE PREFERRED EMBODIMENTS

Figure 1B:
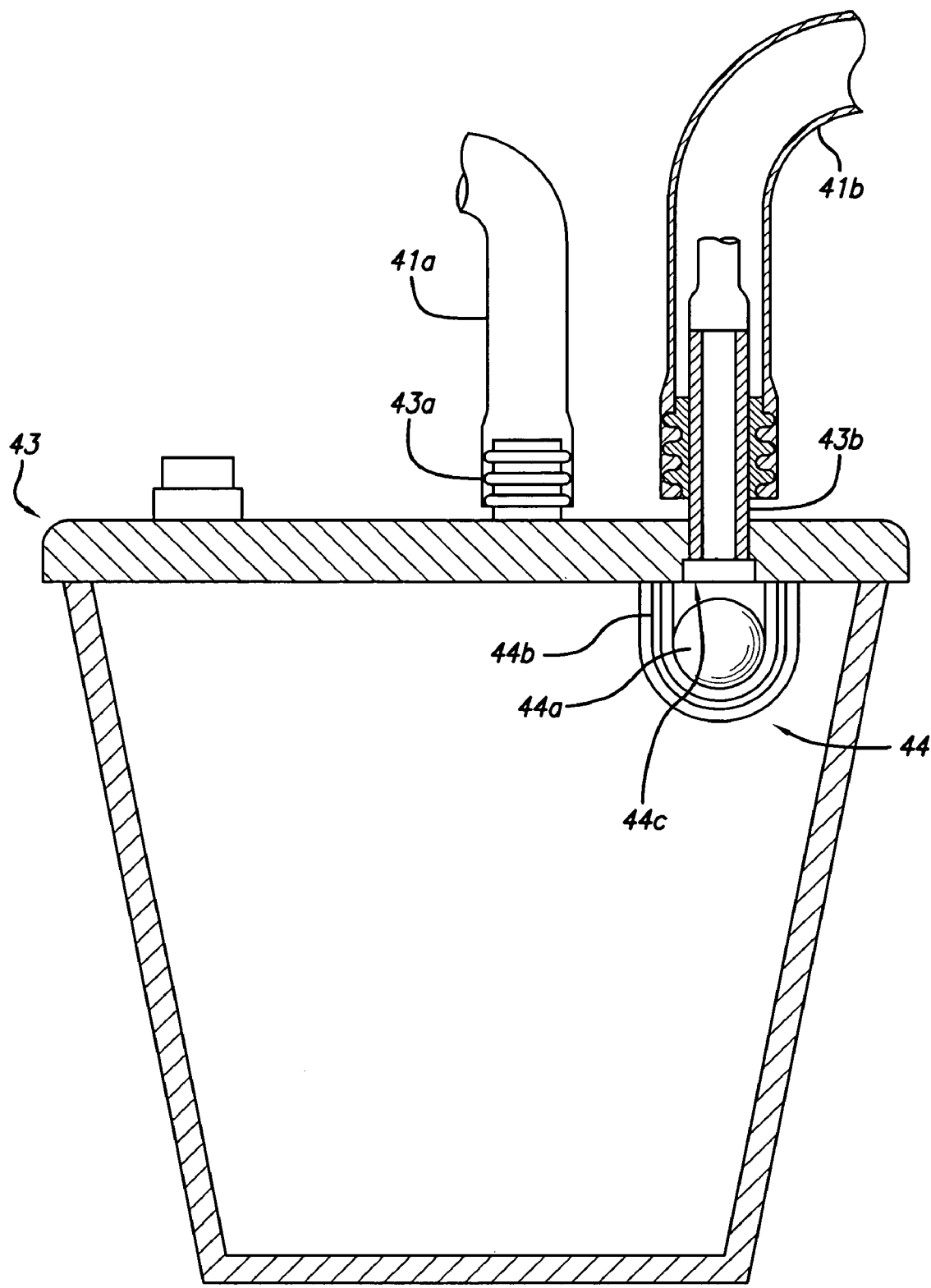
FIG. 1B is a sectional elevational detailed view of an embodiment of the collection system of FIG. 1A.

In accordance with the present invention, a wound treatment appliance is provided for treating a wound by applying reduced pressure (i.e., pressure that is below ambient atmospheric pressure) to the site of the wound to be treated in a controlled manner for a selected time period in a manner that overcomes the disadvantages of currently existing apparatus. As illustrated in FIG. 1A, one embodiment of a first version of the wound treatment appliance 10 is comprised of a wound covering device 20 and a vacuum system (illustrated schematically and generally designated 50). In this embodiment, the vacuum system 50 is generally comprised of a reduced pressure supply source (illustrated schematically and generally designated 30), which is used to produce a supply of reduced pressure for use with the wound covering device 20, and reduced pressure supply means (illustrated schematically and generally designated 40). The reduced pressure supply means 40, which is described in more detail below, is used to connect the wound treatment device 20 to the reduced pressure supply source 30 that provides a supply of reduced pressure to the wound treatment device 20, so that the area under the wound treatment device 20 in the area of the wound 61 is supplied with reduced pressure by the reduced pressure supply source 30.

In the embodiment of the first version of the invention illustrated in FIG. 1A, the wound covering device 20 is further comprised of an impermeable overlay 21, a stopper 22, a suction drain 23, suction drain sealing means (which are discussed in more detail below), and reduced pressure supply means (which are also discussed in more detail below). In this embodiment, the impermeable overlay 21 has a top end 21a having an opening therein and a bottom end 21b having an opening therein. The bottom end 21b is positioned over the wound 60 on the tissue 71 surrounding the wound 60 so that the impermeable overlay 21 encloses the wound 60 and forms an approximately hermetic seal with such tissue 71. It is to be noted that this hermetic seal may provide for a relatively small degree of leakage, so that outside air may enter the area of the wound 61, as long as the degree of leakage is small enough so that the vacuum system 50 can maintain the desired degree of reduced pressure under the impermeable overlay 21 in the area of the wound 61. In addition, the impermeable overlay 21 is sufficiently rigid so that it supports the stopper 22 and is supported out of contact from the wound 60. In this embodiment, the impermeable overlay 21 is comprised of an overlay top portion 21c and an overlay bottom portion 21d, wherein the overlay bottom portion 21d is approximately conical in shape, having a larger opening at one end 21b and a smaller opening at the other end 21e, the larger opening being the bottom end 21b opening of the impermeable overlay 21. In this embodiment, the overlay top portion 21c is approximately in the shape of a cylindrical tube having an opening at each end 21a, 21e, one opening being the top end 21a opening of the impermeable overlay 21 and the other opening 21e being adjacent to the smaller opening 21e of the overlay bottom portion 21d. In this embodiment, the overlay bottom portion 21d further comprises a flange portion 21f that is adjacent to and extends around the perimeter of the exterior portion of the bottom end 21b opening of the impermeable overlay 21. The flange portion 21f generally dissipates the force exerted by the perimeter of the bottom end 21b opening on the tissue 71 surrounding the wound 60, the force being created by the reduced pressure in the area of the wound 61 under the impermeable overlay 21. In other embodiments of this first version of the invention, the impermeable overlay 21 may be of almost any shape that may be adaptable for treating a wound, as long as the impermeable overlay 21 is rigid enough to support the stopper 22, to support the impermeable overlay 21 away from contact with the wound 60, and has a bottom end 21b that is adapted to make an approximately hermetic seal with the tissue 71 surrounding the wound 60. For example, the impermeable overlay 121 may be in the shape illustrated in FIG. 2 in some embodiments, as described in more detail below. As another example, and in other embodiments, the impermeable overlay 221 may be in the shape illustrated in FIG. 3, or the impermeable overlay 321 may be in the shape illustrated in FIG. 4, in each case as described in more detail below. Referring again to the embodiment illustrated in FIG. 1A, the preferred shape and size of the impermeable overlay 21 is dependent upon the type and size of the wound 60, the location on the body on which the wound 60 is located, the desired wound 60 treatment, and the individual preference of the user of the appliance 10.

It is to be noted, however, that the top end 21a opening of the impermeable overlay 21 need not be circular in shape. For example, the top end 21a opening may be of elliptical, square, rectangular, pentagonal, hexagonal, or any other shape, as long as the shape is adapted to the shape of the stopper 22 so that an approximately hermetic seal is made between the top end 21a opening and the stopper 22, as described in more detail below. The preferred shape of the top end 21a opening, however, is circular. In addition, it is to be noted that the bottom end 21b opening of the impermeable overlay 21 need not be circular in shape. For example, the bottom end 21b opening may be of elliptical, square, rectangular, pentagonal, hexagonal, or any other shape, as long as the perimeter of the bottom end 21b opening is adapted to create an approximately hermetic seal with the tissue 71 surrounding the wound 60. The preferred shapes for the bottom end 21b opening, however, are circular and elliptical. It is also to be noted that in other embodiments of this first version of the invention, the overlay bottom portion 21d may be further comprised of a padding material (not illustrated) placed between the perimeter of the bottom end 21b opening and the tissue 71 surrounding the wound 60. In embodiments including a flange portion 21f, the padding material may be placed between the perimeter of the flange portion 21f and the tissue 71 surrounding the wound 60. This padding material may be comprised of almost any soft and pliable material suitable for medical use, such as cotton, gauze, fabrics, and inflated pillows and similar figures constructed of polymers. In the embodiment illustrated in FIG. 1A, the perimeter of the bottom end 21b opening of the impermeable overlay 21 is sealed to the tissue 71 surrounding the wound 60 using an adhesive tape 25. In some of these embodiments, the adhesive tape 25 may only be used to hold the impermeable overlay 21 in place in the event reduced pressure is lost in the area of the wound 61 under the impermeable overlay 21. In other embodiments, the tissue sealing means may be the reduced pressure maintained in the area of the wound 61 under the wound covering device 20. In other embodiments, the tissue sealing means may be an adhesive applied to the perimeter of the bottom end 21b opening. In yet other embodiments, the tissue sealing means may be a stretch fabric (not illustrated) that covers the wound covering device 20 and is wrapped around a portion of the body of the patient in the area of the wound 60. For example, if the wound 60 is located on a patient's leg, the wound covering device 20 may be placed over the wound 60, and the stretch fabric may be wrapped around the portion of the leg where the wound 60 is located, covering the wound covering device 20 in the wrapping process. The stretch fabric may be comprised of any suitable material, such as an ace bandage, stretch netting, or other clothing-type item made of a stretchable material, such as SPANDEX. The preferred tissue sealing means is dependent upon the type and size of the wound 60, the location on the body on which the wound 60 is located, the desired wound 60 treatment, and the individual preference of the user of the appliance 10. As described above, it is to be noted that the hermetic seal provided by the tissue sealing means may allow for a relatively small degree of leakage in some embodiments, so that outside air may enter the area of the wound 61, as long as the degree of leakage is small enough so that the vacuum system 50 can maintain the desired degree of reduced pressure under the impermeable overlay 21 in the area of the wound 61.

In the various embodiments of this first version of the invention, as illustrated in FIG. 1A, the impermeable overlay 21 may be comprised of almost any medical grade rigid or semi-rigid material that is currently known in the art or that may be developed in the art in the future, as long as such material fluid liquid-impermeable, suitable for purposes of wound treatment (e.g., can be sterilized and does not absorb significant amounts of wound exudate), and is capable of forming an adequate gas-impermeable and a liquid-impermeable barrier with the surface of the body at the site of the wound 60. For example, the impermeable overlay 21 may be comprised of glass, wood, metal, polypropylene, polyvinyl chloride, polycarbonate, polysulfone, plastics, and other rigid and semi-rigid polymer materials, or a combination of all such materials. Preferably, the impermeable overlay 21 is comprised of polycarbonate. It is to be noted that in various embodiments of this first version of the invention, the impermeable overlay 21 may be constructed in whole or in part of gas-permeable materials, allowing limited amounts of oxygen and other gases to penetrate the impermeable overlay 21 so that the wound 60 under the impermeable overlay 21 can "breathe." It is also to be noted that all portions of the impermeable overlay 21 are preferably constructed of one type of polymer material, such as polycarbonate. The impermeable overlay 21 may be constructed using any suitable means currently known in the art or that may be developed in the art in the future. For example, an impermeable overlay 21 constructed of polypropylene may be manufactured by means of injection molding.

In the embodiment of the first version of the invention illustrated in FIG. 1A, the wound covering device 20 is also comprised of a stopper 22, which has a port 22a therein. In this embodiment, the stopper 22 is removably positioned in the top end 21a opening of the impermeable overlay 21, forming an approximately hermetic seal with the top end 21a opening of the impermeable overlay 21. In this embodiment, the stopper 22 is approximately in the shape of a cylinder being tapered along its longitudinal axis so that one base 22b of the cylinder has a smaller diameter than the other base 22c. The smaller diameter base 22b of the stopper 22 is within the volume of the impermeable overlay 21 and the larger diameter base 22c of the stopper 22 is outside the volume of the impermeable overlay 21 when the stopper 22 is removably positioned in the top end 21a opening of the impermeable overlay 21. In other embodiments, the stopper 22 may have other shapes, as long as the shape of the stopper 22 is adapted to form an approximately hermetic seal with the top end 21a opening of the impermeable overlay 21. In some embodiments, the approximately hermetic seal with the top end 21a opening is made by contacting the stopper 22 along its entire perimeter on its outside surface adjacent to the top end 21a opening with the interior surface of the top end 21a opening. In other embodiments, the approximately hermetic seal may be also be made (or assisted) by applying an adhesive or other fluid-impermeable substance, such as a petroleum-based jell or anhydrous lanolin, to such surfaces. Preferably, the stopper 22 has a shape so that only a relatively small portion of the surface of the stopper 22 is wedged against the interior surface of the top end 21a opening of the impermeable overlay 21 and the stopper 22 may be easily removed from the top end 21a opening of the impermeable overlay 21. More preferred, the stopper 22 has the approximate shape illustrated in FIG. 1A and the top end 21a opening of the impermeable overlay 21 is in the approximate shape of a circle. In the embodiment of the first version of the invention illustrated in FIG. 1A, the port 22a in the stopper 22 is approximately cylindrical in shape. In other embodiments, the port 22a may have another shape. For example, the port 22a may have a cross-section that is of elliptical, square, rectangular, pentagonal, hexagonal, or another shape, as long as the port 22a is adapted to provide an approximately hermetic seal with the suction drain 23, as described in more detail below. Preferably, the port 22a is approximately cylindrical in shape.

In the various embodiments of this first version of the invention, as illustrated in FIG. 1A, the stopper 22 may be comprised of almost any medical grade material that is currently known in the art or that may be developed in the art in the future, as long as such material is liquid-impermeable, suitable for purposes of wound treatment (e.g., can be sterilized and does not absorb significant amounts of wound exudate), and is capable of forming an adequate gas-impermeable and a liquid-impermeable barrier with the top end 21a opening. For example, the stopper 22 may be comprised of rubber (including neoprene), wood, cork, glass, metal, silicone, polypropylene, polyvinyl chloride, plastics, rubber, and other polymer materials, or a combination of such materials. Preferably, the stopper 22 is comprised of silicone. The stopper 22 may be constructed using any suitable means currently known in the art or that may be developed in the art in the future. For example, a stopper 22 constructed of polypropylene may be manufactured by means of injection molding.

In the embodiment of the first version of the invention illustrated in FIG. 1A, the wound covering device 20 is also comprised of a suction drain 23 and suction drain sealing means, which are described in more detail below. In this embodiment, the suction drain 23 is further comprised of a bottom drain portion 23a extending into the area of the wound 61 under the impermeable overlay 21 from a top drain portion 23b positioned within the port 22a in the stopper 22. In this embodiment, the top drain portion 23b and the bottom drain portion 23a of the suction drain 23 are comprised of flexible tubing. In other embodiments, portions of the top drain portion 23b and the bottom drain portion 23a of the suction drain 23 may be comprised of other materials, such as rigid or semi-rigid polymers, plastics, rubber, silicone, and combinations of such materials. In yet other embodiments, the top drain portion 23b and the bottom drain portion 23a may have different cross-sectional shapes, such as elliptical, square, rectangular, pentagonal, hexagonal, or other shapes, as long as the suction drain 23 is adapted to provide an approximately hermetic seal with the port 22a, as described in more detail below. In still other embodiments, the bottom drain portion 23a of the suction drain 23 may be further comprised of wound suction means that may be used to remove debris, exudate and other matter from the wound 60. In the embodiment illustrated in FIG. 1A, the wound suction means is comprised of a distal portion 23a' of the tubing comprising the bottom drain portion 23a having a plurality of perforations 23a" in the surface of the distal portion 23a'. In other embodiments, the distal portion 23a' of the bottom drain portion 23a may have more or fewer perforations 23a", may have different sizes and shapes of perforations 23a", and may extend along different portions of the bottom drain portion 23a.

Figure 2:
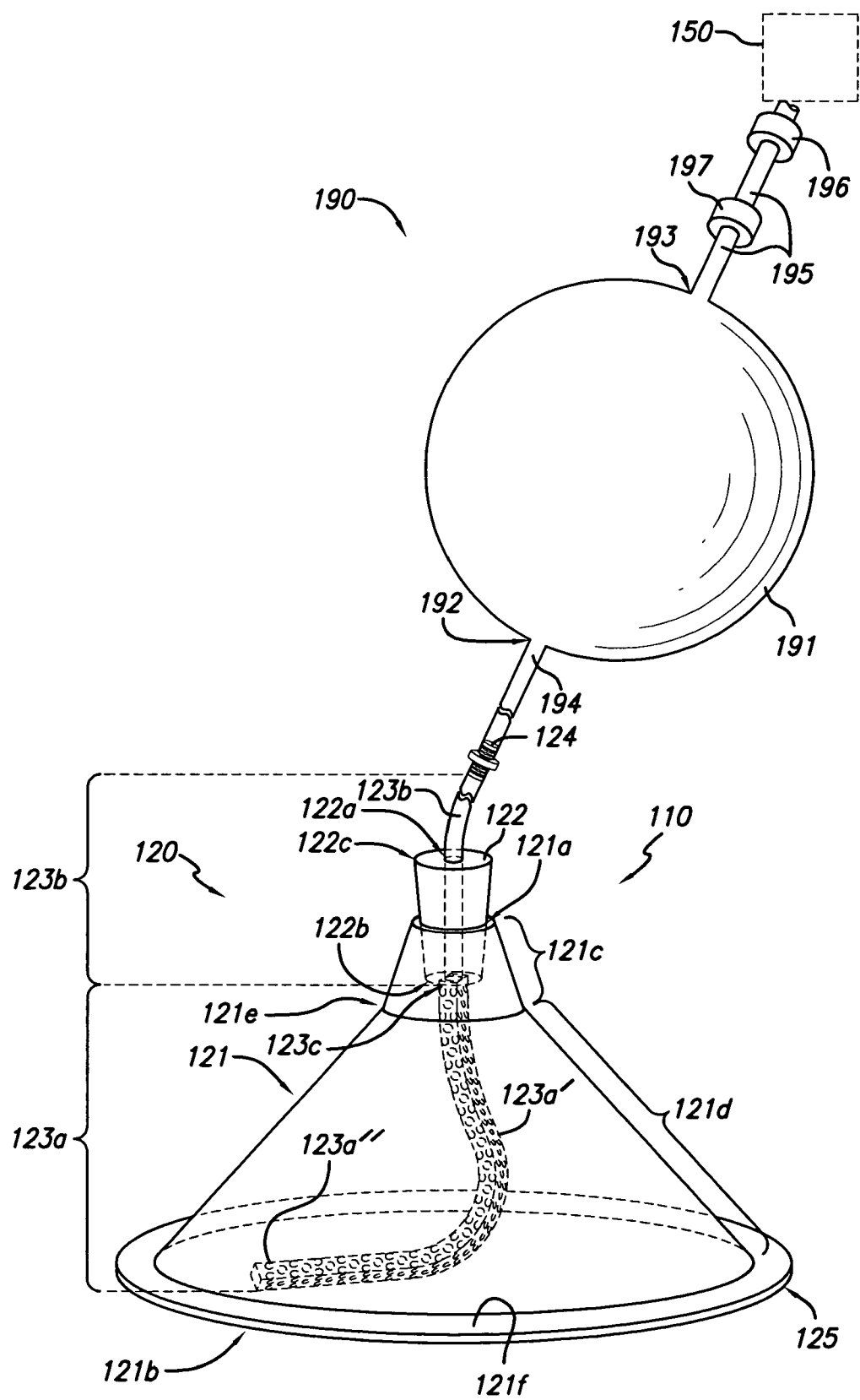
FIG. 2 is a perspective view of another embodiment of a wound treatment appliance of the first version of the present invention, as viewed from the side of and above the appliance (as the wound covering device of the appliance would be oriented when placed on the body of a patient)

In yet other embodiments of this first version of the invention, as illustrated in FIG. 2, the wound suction means may be comprised of a wound suction member 123a', which constitutes the entire bottom drain portion 123a in this embodiment, and wound suction member attachment means, which are described in more detail below. In this embodiment, the wound suction member 123a' is approximately rectangular in shape, has a hollow interior, is constructed of a flexible material, and has a plurality of perforations 123a" in its surface. In other embodiments, the wound suction member 123a' may have almost any shape or combination of shapes (e.g., circular, elliptical, square, pentagonal, or hexagonal), be of almost any size relative to the remaining bottom drain portion 123a (e.g., may have a cross-section smaller or larger than the remaining bottom drain portion 123a), may have more or fewer perforations 123a", may have different sizes and shapes of perforations 123a", may extend along different portions of the bottom drain portion 123a, and may be constructed in whole or in part of materials that are not flexible. For example, in the embodiment of the suction drain 227 illustrated in FIG. 3, the suction member 227a' is approximately circular in shape, has larger perforations 227a", extends along a lesser portion of the bottom drain portion 227a, and is comprised of a semi-rigid material. It is to be noted that in various embodiments of this first version of the invention, and referring once again to FIG. 1A, the top drain portion 23b and the bottom drain portion 23a of the suction drain 23 may be produced with a length greater than that illustrated. In such embodiments, the user of the suction drain 23 may cut the suction drain 23 to the appropriate length. For example, in the embodiment illustrated in FIG. 2, the suction member 123a' as manufactured may be longer than the length illustrated, and prior to use of the suction drain 123, the user may cut a portion of the distal end of the suction member 123a' off so that the suction member 123a' is of the desired length. In embodiments that have a suction member 123a', as is illustrated in FIG. 2, the wound suction member attachment means, which is used to connect the suction member 123a' to the remaining portion of the bottom drain portion 123a in a manner so that the remaining bottom drain portion 123a is in fluid communication with the wound suction member 123a', may be of almost any suitable means. For example, the wound suction member attachment means may be an adhesive in some embodiments and a fastening collar in other embodiments. In still other embodiments, the suction member 123a' may be fused or welded to the remaining portion of the bottom drain portion 123a. In yet other embodiments, the suction member 123a' and the remaining portion of the bottom drain portion 123a may be fabricated as a single piece.

In some embodiments of this first version of the invention, as illustrated in FIG. 1A, the top drain portion 23b may extend beyond the top larger base 22c of the stopper 22 into the area outside the volume of the impermeable overlay 21. In other embodiments, the top drain portion 23b of the suction drain 23 is further comprised of tubing connection means, which may be used to removably connect the reduced pressure supply means 40, which are described in more detail below, to the top drain portion 23b of the suction drain 23. In the embodiment of the invention illustrated in FIG. 1A, the tubing connection means is a variable descending diameter adapter 24 (commonly referred to as a "Christmas tree" adapter) that is placed into the interior volume of the top drain portion 23b at its distal end. In other embodiments, the tubing connection means may be clamps, fastening collars, and other fasteners. In yet other embodiments, the top drain portion 23b may be fused or welded to the reduced pressure supply means 40. In still other embodiments, the top drain portion 23b and the portion of the reduced pressure supply means 40 adjacent to the top drain portion 23b may be fabricated as a single piece.

Figure 4:
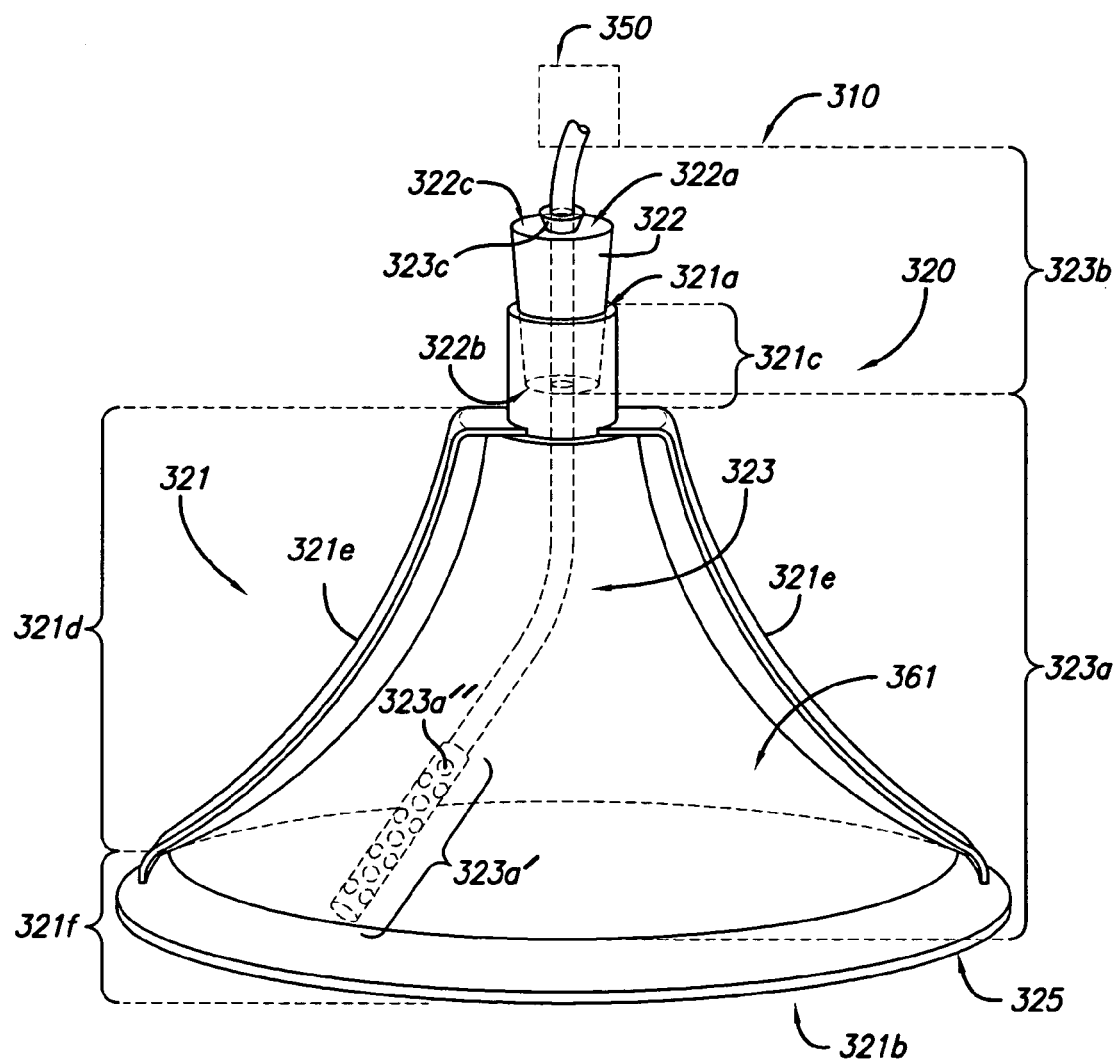
FIG. 4 is a perspective view of another embodiment of a wound treatment appliance of the first version of the present invention, as viewed from the side of and above the appliance (as the wound covering device of the appliance would be oriented when placed on the body of a patient)

In the embodiment of the first version of the invention illustrated in FIG. 1A, the suction drain sealing means is used to provide an approximately hermetic seal between the suction drain 23 and the stopper 22. In the illustrated embodiment, the suction drain sealing means is a drain sealing portion 23c that is located on the suction drain 23 at approximately the connection of the top drain portion 23b to the bottom drain portion 23a. In this embodiment, the drain sealing portion 23c is approximately conical in shape, with the apex of the drain sealing portion 23c facing toward the top drain portion 23b. In other embodiments, the drain sealing portion 23c may be of other shapes, such as spherical or ellipsoidal, as long as the drain sealing portion 23c is adapted to make an approximately hermetic seal with the port 22a of the stopper 22, as described in more detail below. The drain sealing portion 23c may be fabricated as a part of the suction drain 23 or it may be a separate component that is attached to the suction drain 23 at the appropriate location. For example, the drain sealing portion 23c may be a collar that has a slightly larger diameter than the suction drain 23, which is attached to the suction drain 23 by means of an adhesive. In other embodiments, such as that illustrated in FIG. 2, the wound suction member attachment means may also act as the drain sealing portion 123c. In the embodiment illustrated in FIG. 1A, the distal end of the top drain portion 23b of the suction drain 23 is inserted into the port 22a in the smaller diameter base 22b of the stopper 22, and is then pulled through until the drain sealing portion 23c is seated against the port 22a at the smaller diameter base 22b of the stopper 22. When the drain sealing portion 23c is wedged against the port, an approximately hermetic seal is formed. When the user of the appliance 10 desires to cleanse the wound 60, the top drain portion 23b is pushed toward the wound 60, and may be moved in a manner so that the bottom drain portion 23a (and especially the distal portion 23a') is moved about the wound 60 and the area of the wound 61 so that debris, exudate and other material can be drawn through the perforations 23a" and be expelled out the distal end of the top portion 23b of the suction drain 23 by the reduced pressure produced by the reduced pressure supply source 30. In addition, while the seal between the suction drain 23 and the port 22a is broken, fluids (such as water, saline solutions, and medications) may be injected into the area of the wound 61 under the impermeable overlay 21 by using a hypodermic or similar type of syringe. In other embodiments of the invention, as illustrated in FIG. 4, the drain sealing portion 323c may be located on the top drain portion 323b above the port 322a entrance on the larger diameter base 322c of the stopper 322. In this embodiment, the approximately hermetic seal is made at the larger diameter base 322c of the stopper 322, and the suction drain 323 is pulled away from the stopper 322 to allow for movement of the bottom drain portion 323a in the area of the wound 361 under the impermeable overlay 321. Referring again to the embodiment illustrated in FIG. 1A as an example, in other embodiments of this first version of the invention the approximately hermetic seal may be made by a portion of the top drain portion 23b of the suction drain 23 having an outside diameter only slightly smaller than the inside diameter of the port 22a so that the suction drain 23 fits tightly against the inside surface of the port 22a. It is to be noted that the shape and size of the entrance of the port 22a, the suction drain 23, and the drain sealing portion 23c are adapted so that an approximately hermetic seal can be made between the suction drain 23 and the port 22a.

Thus, in the preferred embodiments in this first version of the invention, as illustrated in FIG. 1A, the wound 60 may be cleansed or otherwise treated without removing the impermeable overlay 21 from the tissue surrounding the wound 71. For example, as described above in the immediately preceding paragraph, the suction drain 23 may be moved relative to the port 22a in the stopper 22. In addition, where the stopper 22 is removably positioned within the top end 21a opening in a manner so that the stopper 22 may be easily removed from the top end 21a opening, the stopper 22 may also be removed from the impermeable overlay 21. This allows for an even greater degree of access to the wound 60 and the area of the wound 61 under the impermeable overlay 21. For example, for a top end 21a opening of sufficient diameter, it may be possible to irrigate the wound 60 or use other tools for treatment of the wound 60, such as a scalpel to remove tissue at the site of the wound 60, without the need to remove the impermeable overlay 21.

In the embodiment of the first version of the invention illustrated in FIG. 1A, the reduced pressure supply source 30 of the vacuum system 50, which produces a source of reduced pressure or suction that is supplied to the wound covering device 20, includes a vacuum pump 31, a control device 32, a filter 33, and a power source 34. Although the preferred means of producing the reduced pressure or suction is a vacuum pump 31, in other embodiments of this first version of the invention other means may be used, such as an outlet port of a centralized hospital vacuum system or the vacuum system 190 described in more detail below and illustrated in connection with FIG. 2 or the vacuum system 450 described in more detail below and illustrated in connection with FIG. 2. In the illustrated embodiment, predetermined amounts of suction or reduced pressure are produced by the vacuum pump 31. The vacuum pump 31 is preferably controlled by a control device 32, such as a switch or a timer that may be set to provide cyclic on/off operation of the vacuum pump 31 according to user-selected intervals. Alternatively, the vacuum pump 31 may be operated continuously without the use of a cyclical timer. In addition, in some embodiments the control device 32 may provide for separate control of the level of reduced pressure applied to the wound 60 and the flow rate of fluid aspirated from the wound 60. In these embodiments, relatively low levels of reduced pressure may be maintained in the area of the wound 61 under the wound covering device 20, while still providing for the removal of a relatively large volume of exudate from the wound 60. A filter 33, such as a micropore filter, is preferably attached to the inlet of the vacuum pump 31 to prevent potentially pathogenic microbes or aerosols from contaminating, and then being vented to atmosphere by, the vacuum pump 31. In other embodiments, the filter 33 may also be a hydrophobic filter that prevents any exudate from the wound from contaminating, and then being vented to atmosphere by, the vacuum pump 31. The power source 34 may be any source of energy currently known in the art or that may be developed in the art in the future that may be used to power the vacuum pump 31. For example, in some embodiments, the power source 34 may be electric current produced from a standard power outlet, such as a 110 volt, 60 hertz, power outlet in the United States, that passes through a standard plug and cord that are well known in the art. In other embodiments, the power source 34 may be a fuel cell or battery. It is to be noted that in other embodiments of the invention, the reduced pressure supply source 30 may not have a filter 33 or a control 32 or any combination of the same.

In the embodiment of the first version of the invention illustrated in FIG. 1A, the reduced pressure supply means 40 of the vacuum system 50, which is used to connect the reduced pressure supply source 30 to the suction drain 23 so that reduced pressure is supplied to the area of the wound 61 under the impermeable overlay 21, is comprised of at least one tubing member 41. In this embodiment, the at least one tubing member 41 is sufficiently flexible to permit movement of the at least one tubing member 41, but is sufficiently rigid to resist constriction when reduced pressure is supplied to the suction drain 23 or when the location of the wound 60 is such that the patient must sit or lie upon the at least one tubing member 41 or upon the wound covering device 20. In the embodiment illustrated in FIG. 1A, the at least one tubing member 41 is connected to the suction drain 23 by inserting one end of the at least one tubing member 41 into the variable diameter adapter 24, which represents the tubing connection means in this embodiment. It is to be noted that in other embodiments of this first version of the invention, the at least one tubing member 41 may be connected to the suction drain 23 using any suitable means currently known in the art or developed in the art in the future. Examples include the tubing connection means discussed above. Alternatively, the suction drain 23 and the at least one tubing member 41 may be fabricated as a single piece. Similar means may be used to connect the other end of the at least one tubing member 41 to the vacuum pump 31 or other reduced pressure supply source 30 providing the reduced pressure.

In the embodiment illustrated in FIG. 1A, the reduced pressure supply means 40 further comprises a fluid collection system, generally designated 42, that is interconnected between the suction pump 31 and the suction drain 23 to remove and collect any exudate that may be aspirated from the wound 60 and collected by the suction drain 23. The suction drain 23 functions to actively draw fluid or exudate from the wound 60. Collection of exudate in a fluid collection system 42 intermediate the pump 31 and the suction drain 23 is desirable to prevent clogging of the vacuum pump 31. The fluid collection system 42 is comprised of a fluid-impermeable collection container 43 and a shutoff mechanism 44, which is described in more detail below in connection with FIG. 1B. In various embodiments of this first version of the invention, the container 43 may be of any size and shape capable of intercepting and retaining a predetermined amount of exudate. Many examples of such containers are available in the relevant art. The container in this embodiment of the invention is illustrated in side elevational schematic view in FIG. 2A, said container 43 having two openings 43a, 43b in the top of the container 43. Referring to FIG. 2B, which is the preferred embodiment of the container 43, the container 43 includes a first port 43a at the top opening of the container 43 for sealed connection to tubing member 41a, where the other end of the tubing member 41a is connected to the suction drain 23. The first port 43a enables suction to be applied to the suction drain 23 through the tubing 41a and also enables exudate from the wound 60 covered by the impermeable overlay 21 to be drained into the container 43. The container 43 provides a means for containing and temporarily storing the collected exudate. A second port 43b is also provided on the top of the container 43 to enable the application of suction from the vacuum pump 31. The second port 43b of the collection system 42 is connected to the vacuum pump 31 by tubing member 41b. The collection system 42 is sealed generally gas-tight to enable the vacuum pump 31 to supply suction to the suction drain 23 through the collection system 42. In other embodiments of this first version of the invention, the container 43 may also include a fluid impenetrable flexible liner within its volume that is used to collect the exudate in a manner that avoids contaminating the container 43 with pathogenic microbes and other harmful matter present in the exudate. In such case, the flexible liner may be directly connected to the first port 43a and second port 43b in a manner so that no exudate comes into direct contact with the container 43. In this embodiment, the preferred liner is a flexible bag constructed of a polymer material, which is connected to the first port 43a and the second port 43b.

In the embodiment illustrated in FIG. 1A and FIG. 1B, the vacuum system 50 and collection system 42 preferably include a shutoff mechanism for halting or inhibiting the supply of the reduced pressure to the suction drain 23 in the event that the exudate aspirated from the wound 60 exceeds a predetermined quantity. Interrupting the application of suction to the suction drain 23 is desirable to prevent exsanguination in the unlikely event a blood vessel ruptures under the impermeable overlay 21 during treatment. If, for example, a blood vessel ruptures in the vicinity of the wound 60, a shut-off mechanism would be useful to prevent the vacuum system 50 from aspirating any significant quantity of blood from the patient. In the preferred embodiment of the shutoff mechanism 44, as illustrated in FIG. 1B, the shutoff mechanism 44 is a float valve assembly in the form of a ball 44a which is held and suspended within a cage 44b positioned below a valve seat 44c disposed within the opening at the top of the container below the second port 43b that will float upon the exudate and will be lifted against the valve seat 44c as the container 43 fills with exudate. When the ball 44a is firmly seated against the valve seat 44c, the float valve blocks the second port 43b and thereby shuts off the source of suction from the vacuum system 50. In other embodiments of the container 43, other types of mechanisms may also be employed to detect the liquid level within the container 43 in order to arrest operation of the vacuum system 50. In addition, in various embodiments of this first version of the invention, the shutoff mechanism 44 may be comprised of any means that enables the vacuum system 50 to halt the supply of reduced pressure to the suction drain 23 at any time that the volume of exudate from the wound 60 exceeds a predetermined amount. Such means may include mechanical switches, electrical switches operably connected to the vacuum system controller 32, optical, thermal or weight sensors operably connected to the vacuum system controller 32, and any other means that are currently known in the relevant art or that may be developed in the art in the future.

The embodiment of this first version of the invention illustrated in FIG. 1A and FIG. 1B may be operated using a variety of methods. One such method comprises the following steps. First, the suction drain 23 is operably positioned in the port 22a in the stopper 22. Second, the stopper 22 is operably positioned in the top end 21a opening of the impermeable overlay 21. Third, the bottom end 21b of the impermeable overlay 21 is operably placed over the wound 60 in a manner that an approximately hermetic seal is formed with the tissue 71 surrounding the wound 60. Fourth, the suction drain 23 is operably connected to the reduced pressure supply source 50 using the reduced pressure supply means 40. It should be noted that the preceding steps may generally be performed in any order. Fifth, the reduced pressure supply source 50 is operated in a manner so that it provides a supply of reduced pressure to maintain reduced pressure in the area of the wound 61 under the impermeable overlay 21. Sixth, reduced pressure is maintained in the area of the wound 61 under the impermeable overlay 21 until the wound 60 being treated has progressed toward a selected stage of healing. In other embodiments, this method may further comprise the step of removing the stopper 22 from the top end opening of the impermeable overlay 21 to provide access for treatment of the wound 60, as described in more detail above. In yet other embodiments, this method may further comprise the step of manipulating the suction drain 23 so that the suction drain 23 removes debris, fluid and other material from the area of the wound 61 under the impermeable overlay 21, as described in more detail above. In still other embodiments, the reduced pressure is from about 20 mm of Hg below atmospheric pressure to about 125 mm of Hg below atmospheric pressure. In other embodiments, the reduced pressure is applied in a cyclic nature, the cyclic nature providing alternating time periods of application of reduced pressure and without application of reduced pressure. In some of these embodiments, the pressure may be applied for a period of approximately 6 to 8 hours during a period each day when the patient is sleeping.

Another embodiment of the first version of the invention is illustrated in FIG. 2. In this embodiment, the appliance 110 is comprised of a wound covering device 120 and a vacuum system 190. The wound covering device 120 is further comprised of an impermeable overlay 121, a stopper 122, a suction drain 123, suction drain sealing means (which are discussed in more detail below), and reduced pressure supply means (which are also discussed in more detail below). In these embodiments, the impermeable overlay 121 is comprised of an overlay top portion 121c and an overlay bottom portion 121d, wherein the overlay bottom portion 121d is approximately conical in shape, having a larger opening at one end 121b and a smaller opening at the other end 121e, the larger opening being the bottom end 121b opening of the impermeable overlay 121. In this embodiment, the overlay top portion 121c is also approximately conical in shape, having a larger opening at one end 121e and a smaller opening at the other end 121a, the larger opening 121e being adjacent to the smaller opening 121e of the overlay bottom portion 121d and the smaller opening 121a being the top end 121a opening of the impermeable overlay 121. In this embodiment, the overlay bottom portion 121d further comprises a flange portion 121f that is adjacent to and extends around the perimeter of the exterior portion of the bottom end 121b opening of the impermeable overlay 121. The flange portion 121f generally dissipates the force exerted by the perimeter of the bottom end 121b opening on the tissue surrounding the wound (not illustrated) in the same manner as the embodiments of the flange portion 21f of the first version of the invention described above and illustrated in connection with FIG. 1A. It is to be noted that the top end 121a opening and the bottom end 121b opening of the impermeable overlay 121 in various embodiments of the invention illustrated in FIG. 2 may also have substantially the same structure, features, characteristics and operation as the embodiments of the top end 21*a* opening and the bottom end 21*b* opening of the impermeable overlay 21 of the first version of the invention described above and illustrated in connection with FIG. 1A. It is also to be noted that in other embodiments of this first version of the invention illustrated in FIG. 2, the overlay bottom portion 121*d* may be further comprised of a padding material placed between the perimeter of the bottom end 121*b* opening and the tissue surrounding the wound in the same manner that padding material may be included with the embodiments of the overlay bottom portion 21*d* of the first version of the invention described above and illustrated in connection with FIG. 1A. Further, in the embodiment illustrated in FIG. 2, the perimeter of the bottom end 121*b* opening of the impermeable overlay 121 may be approximately hermetically sealed to the tissue surrounding the wound using substantially the same tissue sealing means used to approximately hermetically seal the perimeter of the embodiments of the bottom end 21*b* opening of the impermeable overlay 21 of the first version of the invention to the tissue 71 surrounding the wound 60, as described above and illustrated in connection with FIG. 1A. The impermeable overlay 121 of the embodiment illustrated in FIG. 2 may also be comprised of the same materials and be constructed in the same manner as the embodiments of the impermeable overlay 21 of the first version of the invention described above and illustrated in connection with FIG. 1A.

The stopper 122 (including its smaller base 122*b* and larger base 122*c*) and the port 122*a* in the stopper 122 of the embodiment illustrated in FIG. 2 may also have the substantially the same structure, features, characteristics and operation as the embodiments of the stopper 22 and port 22*a*, respectively, of the first version of the invention described above and illustrated in connection with FIG. 1A. In the embodiment illustrated in FIG. 2, the stopper 122 is removably positioned in the top end 121*a* opening of the impermeable overlay 121, forming an approximately hermetic seal with the top end 121*a* opening of the impermeable overlay 121 in substantially the same manner as in the embodiments of the invention described above and illustrated in connection with FIG. 1A. In the embodiment illustrated in FIG. 2, the approximately hermetic seal with the top end 121*a* opening is made by contacting the stopper 122 along its entire perimeter on its outside surface adjacent to the top end 121*a* opening with the interior surface of the top end 121*a* opening. In addition, the suction drain 123 (including its bottom drain portion 123*a*, top drain portion 123*b*, distal end portion 123*a*', and at least one perforation 123*a*") and suction drain sealing means 123*c* illustrated in FIG. 2 may also have substantially the same structure, features, characteristics and operation as the embodiments of the suction drain 23 (including its bottom drain portion 23*a*, top drain portion 23*b*, distal end portion 23*a*', and at least one perforation 23*a*") and suction drain sealing means 23*c*, respectively, of the first version of the invention described above and illustrated in connection with FIG. 1A. In the embodiment of the suction drain 123 illustrated in FIG. 2, the bottom drain portion 123*a* is comprised of an approximately rectangular wound suction member 123*a*', which constitutes the entire bottom drain portion 123*a* in this embodiment, and wound suction member attachment means, all of which are described in more detail above. Further, the tubing connection means of the embodiment of the invention illustrated in FIG. 2, which may be used to removably connect the reduced pressure supply means 194 to the top drain portion 123*b* of the suction drain 123 may be substantially the same as the embodiments of the tubing connection means described above and illustrated in connection with FIG. 1A. The tubing connection means in the embodiment illustrated in FIG. 2 is a variable descending diameter adapter 124 (commonly referred to as a "Christmas tree" adapter). Similarly, the suction drain sealing means of the embodiment of the invention illustrated in FIG. 2, which may be used to provide an approximately hermetic seal between the suction drain 123 and the stopper 122, may be substantially the same as the embodiments of the suction drain sealing means described above and illustrated in connection with FIG. 1A. In the embodiment illustrated in FIG. 2, the suction drain sealing means is a drain sealing portion 123*c*, which is also the wound suction member attachment means, that is located on the suction drain 123 at approximately the connection of the top drain portion 123*b* to the wound suction member 123*a*'. In the embodiment of the first version of the invention illustrated in FIG. 2, the impermeable overlay 121, the stopper 122, and the suction drain 123 are adapted to work together and operate in the same manner as the embodiments of the impermeable overlay 21, the stopper 22, and the suction drain 23, respectively, as is described above and illustrated in connection with FIG. 1A.

In the embodiment of the first version of the invention illustrated in FIG. 2, the vacuum system 190 is generally comprised of a suction bulb 191 having an inlet port 192 and an outlet port 193, a bulb connection tubing member 194, an exhaust tubing member 195, an exhaust control valve 196, and a filter 197, and a supplemental vacuum system (illustrated schematically and generally designated 150). In this embodiment, the suction bulb 191 is a hollow sphere used to produce a supply of reduced pressure for use with the wound covering device 120. In addition, the suction bulb 191 may also be used to receive and store fluid aspirated from the wound. The inlet port 192 of the suction bulb 191 is connected to one end of the bulb connection tubing member 194, which is connected by tubing connection means to the top drain portion 123*b* at its other end, in a manner so that the interior volume of the suction bulb 191 is in fluid communication with the suction drain 123. In this embodiment, the bulb connection tubing member 194 is sufficiently flexible to permit movement of the bulb connection tubing member 194, but is sufficiently rigid to resist constriction when reduced pressure is supplied to the suction drain 123 or when the location of the wound is such that the patient must sit or lie upon the bulb connection tubing member 194 or upon the wound covering device 120. The outlet port 193 of the suction bulb 191 is connected to the exhaust tubing member 195. In this embodiment, the exhaust tubing member 195 is sufficiently flexible to permit movement of the exhaust tubing member 195, but is sufficiently rigid to resist constriction when reduced pressure is supplied to the suction drain 123. In the illustrated embodiment, the exhaust control valve 196 and the filter 197 are operably connected to the exhaust tubing member 195. In this embodiment, the exhaust control valve 196 is used to regulate the flow of fluids (gases and liquids) to and from the suction bulb 191 and the supplemental vacuum system 150. In embodiments of the invention that do not have a supplemental vacuum system 150, the exhaust control valve 196 regulates flow of fluids to and from the suction bulb 191 and the outside atmosphere. Generally, the exhaust control valve 196 allows fluids to flow out of the suction bulb 191 through the outlet port 193, but not to flow in the reverse direction unless permitted by the user of the appliance 110. Any type of flow control valve may be used as the exhaust control valve 196, as long as the valve is capable of operating in the anticipated environment involving reduced pressure and wound exudate. In this embodiment, the filter 197 is operably attached to the exhaust tubing member 195 between the outlet port 193 of the suction bulb 191 and the exhaust control valve 196. The filter 197 prevents potentially pathogenic microbes or aerosols from contaminating the exhaust control valve 196 (and reduced pressure supply source 150), and then being vented to atmosphere. The filter 197 may be any suitable type of filter, such as a micropore filter. In other embodiments, the filter 197 may also be a hydrophobic filter that prevents any exudate from the wound from contaminating the exhaust control valve 196 (and the supplemental vacuum system 150), and then being vented to atmosphere. In still other embodiments, the filter 197 may perform both functions.

In some embodiments of this first version of the invention illustrated in FIG. 2, the suction bulb 191 may be used to produce a supply of reduced pressure in the following manner. First, the user of the appliance 110 appropriately seals all of the component parts of the appliance 110 in the manner described herein. The user then opens the exhaust control valve 196 and applies force to the outside surface of the suction bulb 191, deforming it in a manner that causes its interior volume to be greatly reduced. When the suction bulb 191 is deformed, the gas in the interior volume is expelled to atmosphere through the outlet port 193, the exhaust tubing member 195, the filter 197, and the exhaust control valve 196. The user then closes the exhaust control valve 196 and releases the force on the suction bulb 196. The suction bulb 191 then expands, drawing fluid from the area of the wound under the wound covering device 120 into the suction bulb 191 through the suction drain 123 and causing the pressure in such area to decrease. To release the reduced pressure, the user of the appliance 110 may open the exhaust control valve 196, allowing atmospheric air into the interior volume of the suction bulb 191. The level of reduced pressure may also be regulated by momentarily opening the exhaust control valve 196.

The suction bulb 191 may be constructed of almost any fluid impermeable flexible or semi-rigid material that is suitable for medical use and that can be readily deformed by application of pressure to the outside surface of the suction bulb 191 by users of the appliance 110 and still return to its original shape upon release of the pressure. For example, the suction bulb 191 may be constructed of rubber, neoprene, silicone, or other flexible or semi-rigid polymers, or any combination of all such materials. In addition, the suction bulb 191 may be of almost any shape, such as cubical, ellipsoidal, or polygonal. The suction bulb 191 may also be of varying size depending upon the anticipated use of the suction bulb 191, the size of the wound covering device 120, use of a supplemental vacuum system 150, the level of reduced pressure desired, and the preference of the user of the appliance 110. In the embodiment of the invention illustrated in FIG. 2, the supplemental vacuum system 150 is connected to the exhaust tubing member 195 and is used to provide a supplemental supply of reduced pressure to the suction bulb 191 and wound covering device 120. In this embodiment, the supplemental vacuum system 150 may have substantially the same structure, features, characteristics and operation of the various embodiments of the vacuum system 50 of the first version of the invention described above and illustrated in connection with FIG. 1A and FIG. 1B. It is to be noted, however, that the supplemental vacuum system 150 need not be used in connection with the vacuum system 190 in other embodiments of the invention.

Another embodiment of the first version of the invention is illustrated in FIG. 4. In this embodiment, the appliance 310 is comprised of a wound covering device 320 and a vacuum system 350. The wound covering device 320 is further comprised of a fluid impermeable flexible overlay 321, a stopper 322, a suction drain 323, suction drain sealing means (which are discussed in more detail below), and reduced pressure supply means (which are also discussed in more detail below). In these embodiments, the impermeable overlay 321 is comprised of an approximately conically-shaped semi-rigid flange portion 321f that is adjacent to the perimeter of the bottom end opening 321b of the impermeable overlay 321, an approximately conically-shaped flexible center portion 321d that extends away from the semi-rigid flange portion 321f, an approximately cylindrical tubular overlay top portion 321c extending away from the flexible center portion 321d, and at least two support members 321e that are each connected at one end to the semi-rigid flange portion 321f and at the other end to the overlay top portion 321c. The distal open end 321a of the overlay top portion 321c is the top end 321a opening of the impermeable overlay 321. In addition, the overlay top end 321c is sufficiently rigid to hold and support the stopper 322, and the at least two support members 321e are sufficiently rigid to support the overlay top end 321c out of contact with the semi-rigid flange portion 321f. The semi-rigid flange portion 321f generally dissipates the force exerted by the perimeter of the bottom end 321b opening on the tissue surrounding the wound (not illustrated) in the same manner as the embodiments of the flange portion 21f of the first version of the invention described above and illustrated in connection with FIG. 1A. It is to be noted that the top end 321a opening and the bottom end 321b opening of the impermeable overlay 321 in various embodiments of the invention illustrated in FIG. 4 may also have substantially the same structure, features, characteristics and operation as the embodiments of the top end 21a opening and the bottom end 21b opening of the impermeable overlay 21 of the first version of the invention described above and illustrated in connection with FIG. 1A. It is also to be noted that in other embodiments of this first version of the invention illustrated in FIG. 4, the semi-rigid flange portion 321f may be further comprised of a padding material placed between the perimeter of the bottom end 321b opening and the tissue surrounding the wound in the same manner that padding material may be included with the embodiments of the overlay bottom portion 21d of the first version of the invention described above and illustrated in connection with FIG. 1A. Further, in the embodiment illustrated in FIG. 4, the perimeter of the bottom end 321b opening of the impermeable overlay 321 may be approximately hermetically sealed to the tissue surrounding the wound using substantially the same tissue sealing means used to approximately hermetically seal the perimeter of the embodiments of the bottom end 21b opening of the impermeable overlay 21 of the first version of the invention to the tissue 71 surrounding the wound 60, as described above and illustrated in connection with FIG. 1A. The impermeable overlay 321 of the embodiment illustrated in FIG. 4 may also be comprised of the same materials and be constructed in the same manner as the embodiments of the impermeable overlay 21 of the first version of the invention described above and illustrated in connection with FIG. 1A.

The stopper 322 (including its smaller base 322b and larger base 322c) and the port 322a in the stopper 322 of the embodiment illustrated in FIG. 4 may also have the substantially the same structure, features, characteristics and operation as the embodiments of the stopper 22 and port 22*a*, respectively, of the first version of the invention described above and illustrated in connection with FIG. 1A. In the embodiment illustrated in FIG. 4, the stopper 322 is removably positioned in the top end 321*a* opening of the impermeable overlay 321, forming an approximately hermetic seal with the top end 321*a* opening of the impermeable overlay 321 in substantially the same manner as in the embodiments of the invention described above and illustrated in connection with FIG. 1A. In the embodiment illustrated in FIG. 4, the approximately hermetic seal with the top end 321*a* opening is made by contacting the stopper 322 along its entire perimeter on its outside surface adjacent to the top end 321*a* opening with the interior surface of the top end 321*a* opening. In addition, the suction drain 323 (including its bottom drain portion 323*a*, top drain portion 323*b*, distal end portion 323*a*', and at least one perforation 323*a*") and suction drain sealing means 323*c* illustrated in FIG. 4 may also have substantially the same structure, features, characteristics and operation as the embodiments of the suction drain 23 (including its bottom drain portion 23*a*, top drain portion 23*b*, distal end portion 23*a*', and at least one perforation 23*a*") and suction drain sealing means 23*c*, respectively, of the first version of the invention described above and illustrated in connection with FIG. 1A. In the embodiment of the suction drain 323 illustrated in FIG. 4, the bottom drain portion 323*a* is comprised of an approximately cylindrical wound suction member 123*a*' and wound suction member attachment means, all of which are described in more detail above. Further, the tubing connection means of the embodiment of the invention illustrated in FIG. 4, which may be used to removably connect the reduced pressure supply means (not illustrated) of the vacuum system 350 to the top drain portion 323*b* of the suction drain 323 may be substantially the same as the embodiments of the tubing connection means described above and illustrated in connection with FIG. 1A. The suction drain sealing means of the embodiment of the invention illustrated in FIG. 4, which may be used to provide an approximately hermetic seal between the suction drain 323 and the stopper 322, may be substantially the same as the embodiments of the suction drain sealing means described above and illustrated in connection with FIG. 1A. In the embodiment illustrated in FIG. 4, the suction drain sealing means is a drain sealing portion 323*c* that is located on the suction drain 323 at a point above the larger base 322*c* of the stopper 322. In the embodiment of the first version of the invention illustrated in FIG. 4, the impermeable overlay 321, the stopper 322, and the suction drain 323 are adapted to work together and operate in the same manner as in the embodiments of the impermeable overlay 21, the stopper 22, and the suction drain 23, respectively, described above and illustrated in connection with FIG. 1A. In the embodiment of the invention illustrated in FIG. 4, the vacuum system 350 may have substantially the same structure, features, characteristics and operation of the various embodiments of the vacuum system 50 of the first version of the invention described above and illustrated in connection with FIG. 1A and FIG. 1B and the vacuum system 190 and supplemental vacuum system 150 described above and illustrated in connection with FIG. 2. In addition, in the embodiment of the invention illustrated in FIG. 4, the means used to connect the vacuum system 350 to the top drain portion 321*b* may be substantially the same as the means used to connect the vacuum system 50 to the top drain portion 23*b*, as described above and illustrated in connection with FIG. 1A and FIG. 1B, and the means used to connect the vacuum system 190 to the top drain portion 123*b*, as described above and illustrated in connection with FIG. 2.

Figure 3:
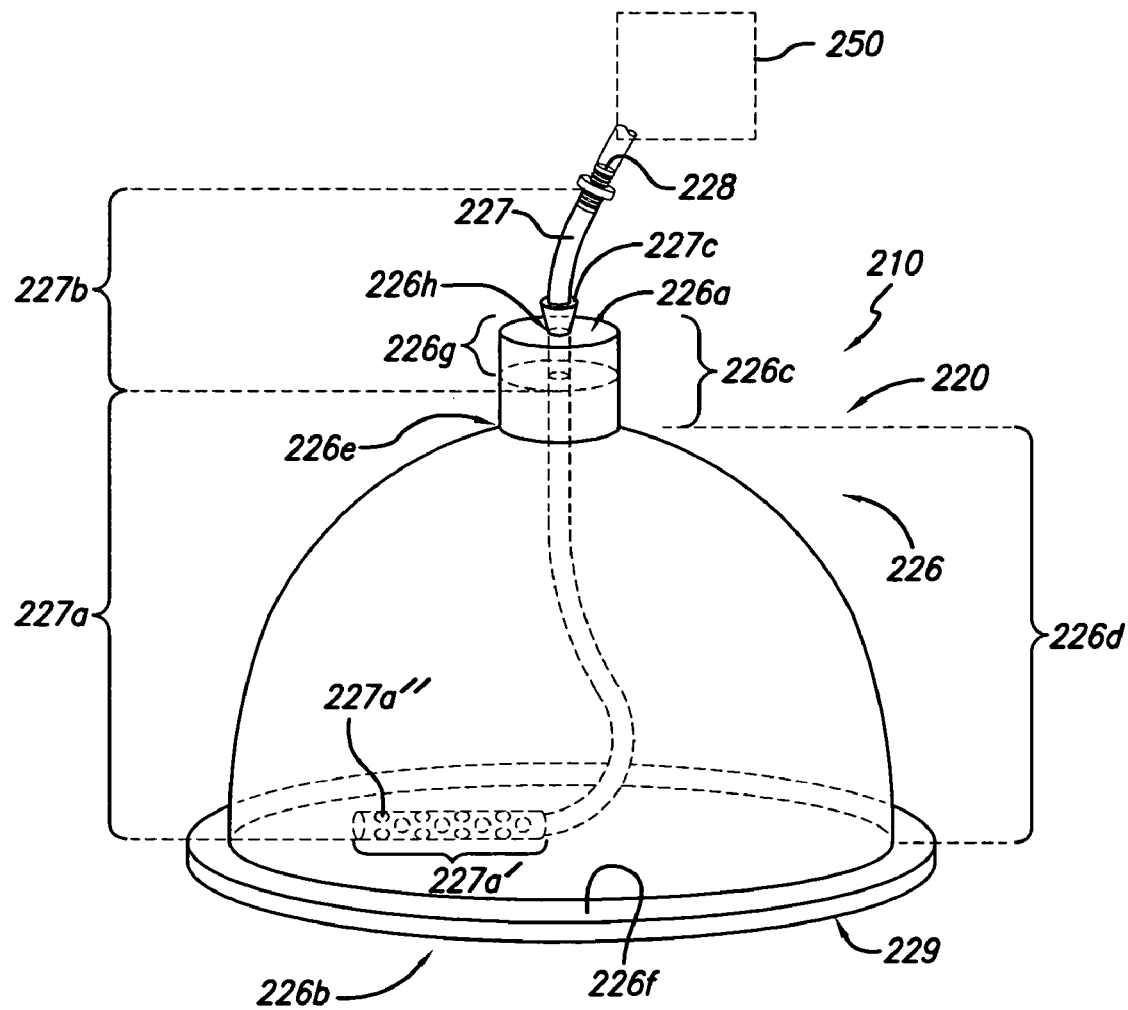
FIG. 3 is a perspective view of an embodiment of a wound treatment appliance of a second version of the present invention, as viewed from the side of and above the appliance (as the wound covering device of the appliance would be oriented when placed on the body of a patient)

An embodiment of a second version of the invention is illustrated in FIG. 3. In this embodiment, the appliance 210 is comprised of a wound covering device 220 and a vacuum system 250. The wound covering device 220 is further comprised of an impermeable overlay 226, a suction drain 227, suction drain sealing means (which are discussed in more detail below), and reduced pressure supply means (which are also discussed in more detail below). In the embodiments of this second version of the invention, as illustrated in FIG. 3, the impermeable overlay 226 is comprised of a port end 226*a* having a port 226*h* therein and a bottom end 226*b* having an opening therein. In the illustrated embodiment, the impermeable overlay 226 is approximately bell-shaped, being comprised of an overlay top portion 226*c* and an overlay bottom portion 226*d*, wherein the overlay bottom portion 226*d* is approximately cup-shaped, having a larger opening at one end 226*b* and a smaller opening at the other end 226*e*, the larger opening being the bottom end 226*b* opening of the impermeable overlay 226. In this embodiment, the overlay top portion 226*c* is approximately cylindrical in shape, having an opening at each end 226*a*, 226*e*, one opening being the port end 226*a* of the impermeable overlay 226 and the other opening 226*e* being adjacent to the smaller opening 226*e* of the overlay bottom portion 226*d*. In this embodiment, the port end 226*a* has port liner portion 226*g*, which has a port 226*h* therein. In this embodiment, the overlay bottom portion 226*d* further comprises a flange portion 226*f* that is adjacent to and extends around the perimeter of the exterior portion of the bottom end 226*b* opening of the impermeable overlay 226. The flange portion 226*f* generally dissipates the force exerted by the perimeter of the bottom end 226*b* opening on the tissue surrounding the wound (not illustrated) in the same manner as the embodiments of the flange portion 21*f* of the first version of the invention described above and illustrated in connection with FIG. 1A. In the various embodiments of this second version of the invention, the impermeable overlay 226 may have substantially the same structure, features characteristics and operation as the impermeable overlays 21, 121, 321 of the first version of the invention described above and illustrated in connection with FIG. 1A, FIG. 2, and FIG. 4, respectively, except that the port end 226*a* in this second version of the invention is substituted for the open ends 21*a*, 121*a*, 321*a*, respectively, of the impermeable overlays 21, 121, 321, respectively, of the first version, and the port 226*h* in the port end 226*a* has substantially the same structure, features, characteristics and operation as the ports 22*a*, 122*a*, 322*a*, respectively, in the stoppers 22, 122, 322, respectively, in the first version of the invention described above and illustrated in connection with FIG. 1A, FIG. 2, and FIG. 4, respectively. In other words, the primary difference between the impermeable overlay 226 in the embodiments of the second version of the invention and those of the first version is that in the second version the port 226*h* is positioned within the port liner portion 226*g* that is a part of the overlay top portion 226*c*, rather than in the stoppers 22, 122, 322, respectively, in the first version of the invention described above and illustrated in connection with FIG. 1A, FIG. 2, and FIG. 4, respectively. In the embodiments of the second version of the invention, the port liner portion 226*g* may be constructed of substantially the same materials as the embodiments of the impermeable overlay 21 or the stopper 22, or any combination thereof, of the first version of the invention described above and illustrated in connection with FIG. 1A. In addition, the port liner portion 226g may be fabricated with the overlay top portion 226c as a single piece in some embodiments of this second version of the invention, or it may be attached to the overlay top portion 226c using any appropriate means in other embodiments. For example, the port liner portion 226g may be attached to the overlay top portion 226c using glues, adhesives, fusion, welding, clamps, and other similar means or any combination of such means.

It is to be noted that in various embodiments of this second version of the invention, and except as noted in the preceding paragraph, the port end 226a and the bottom end 226b opening of the impermeable overlay 226 in various embodiments of the invention illustrated in FIG. 3 may also have substantially the same structure, features, characteristics and operation as the embodiments of the top end 21a opening and the bottom end 21b opening, respectively, of the impermeable overlay 21 of the first version of the invention described above and illustrated in connection with FIG. 1A. It is also to be noted that in other embodiments of this second version of the invention illustrated in FIG. 3, the overlay bottom portion 226d may be further comprised of a padding material placed between the perimeter of the bottom end 226b opening and the tissue surrounding the wound in the same manner that padding material may be included with the embodiments of the overlay bottom portion 21d of the first version of the invention described above and illustrated in connection with FIG. 1A. Further, in the embodiment illustrated in FIG. 3, the perimeter of the bottom end 226b opening of the impermeable overlay 226 may be approximately hermetically sealed to the tissue surrounding the wound using substantially the same tissue sealing means used to approximately hermetically seal the perimeter of the embodiments of the bottom end 21b opening of the impermeable overlay 21 of the first version of the invention to the tissue 71 surrounding the wound 60, as described above and illustrated in connection with FIG. 1A. The impermeable overlay 226 of the embodiment illustrated in FIG. 3 may also be comprised of substantially the same materials and be constructed in the same manner as the embodiments of the impermeable overlay 21 of the first version of the invention described above and illustrated in connection with FIG. 1A.

The port 226h in the port liner portion 226g of the embodiment illustrated in FIG. 3 may also have the substantially the same structure, features, characteristics and operation as the embodiments of the port 22a of the first version of the invention described above and illustrated in connection with FIG. 1A, except that the port 226h of the second version is positioned within the port liner portion 226g, rather than in a stopper. In addition, the suction drain 227 (including its bottom drain portion 227a, top drain portion 227b, distal end portion 227a', and at least one perforation 227a") and suction drain sealing means 227c illustrated in FIG. 3 may also have substantially the same structure, features, characteristics and operation as the embodiments of the suction drain 23 (including its bottom drain portion 23a, top drain portion 23b, distal end portion 23a', and at least one perforation 23a") and suction drain sealing means 23c, respectively, of the first version of the invention described above and illustrated in connection with FIG. 1A. In the embodiment of the suction drain 227 illustrated in FIG. 3, the bottom drain portion 227a is comprised of an approximately cylindrical wound suction member 227a' and wound suction member attachment means, all of which are described in more detail above. Further, the tubing connection means of the embodiment of the invention illustrated in FIG. 3, which may be used to removably connect the reduced pressure supply means (not illustrated) of the vacuum system 250 to the top drain portion 227b of the suction drain 227 may be substantially the same as the embodiments of the tubing connection means described above and illustrated in connection with FIG. 1A. The suction drain sealing means of the embodiment of the invention illustrated in FIG. 3, which may be used to provide an approximately hermetic seal between the suction drain 227 and the port liner portion 226g, may be substantially the same as the embodiments of the suction drain sealing means described above and illustrated in connection with FIG. 1A. In the embodiment illustrated in FIG. 3, the suction drain sealing means is a drain sealing portion 227c that is located on the suction drain 227 at a point above the port liner portion 226g. In the embodiment of the second version of the invention illustrated in FIG. 3, the impermeable overlay 226, the port liner portion 226g, and the suction drain 227 are adapted to work together and operate in the same manner as in the embodiments of the impermeable overlay 21, the stopper 22, and the suction drain 23, respectively, described above and illustrated in connection with FIG. 1A. In the embodiment of the invention illustrated in FIG. 3, the vacuum system 250 may have substantially the same structure, features, characteristics and operation of the various embodiments of the vacuum system 50 of the first version of the invention described above and illustrated in connection with FIG. 1A and FIG. 1B and the vacuum system 190 and supplemental vacuum system 150 described above and illustrated in connection with FIG. 2. In addition, in the embodiment of the invention illustrated in FIG. 3, the means used to connect the vacuum system 250 to the top drain portion 277b may be substantially the same as the means used to connect the vacuum system 50 to the top drain portion 23b, as described above and illustrated in connection with FIG. 1A and FIG. 1B, and the means used to connect the vacuum system 190 to the top drain portion 123b, as described above and illustrated in connection with FIG. 2.

The embodiment of this second version of the invention illustrated in FIG. 3 may be operated using a variety of methods. One such method comprises the following steps. First, the suction drain 227 is operably positioned in the port 226h in the port liner portion 226g. Second, the bottom end 226b of the impermeable overlay 266 is operably placed over the wound in a manner that an approximately hermetic seal is formed with the tissue surrounding the wound in the manner described above. Third, the suction drain 227 is operably connected to the reduced pressure supply source 250 using the reduced pressure supply means. It should be noted that the preceding steps may generally be performed in any order. Fourth, the reduced pressure supply source 250 is operated in a manner so that it provides a supply of reduced pressure to maintain reduced pressure in the area of the wound under the impermeable overlay 226. Fifth, reduced pressure is maintained in the area of the wound under the impermeable overlay 226 until the wound being treated has progressed toward a selected stage of healing. In other embodiments, this method may further comprise the step of manipulating the suction drain 227 so that the suction drain 227 removes debris, fluid and other material from the area of the wound under the impermeable overlay 226, as described in more detail above and illustrated in connection with FIG. 1A. In still other embodiments, the reduced pressure is from about 20 mm of Hg below atmospheric pressure to about 125 mm of Hg below atmospheric pressure. In other embodiments, the reduced pressure is applied in a cyclic nature, the cyclic nature providing alternating time periods of application of reduced pressure and without application of reduced pressure. In some of these embodiments, the pressure may be applied for a period of approximately 6 to 8 hours during a period each day when the patient is sleeping.

Figure 5A:
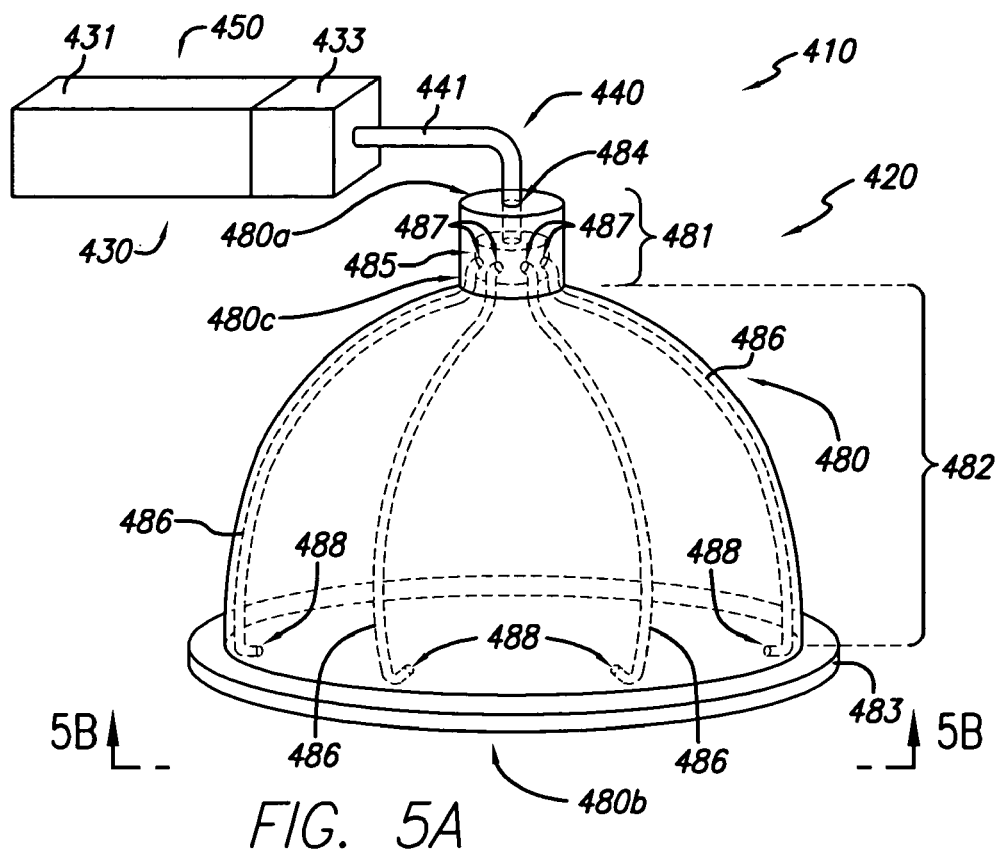
FIG. 5A is a perspective view of an embodiment of a wound treatment appliance of a third version of the present invention, as viewed from the side of and above the appliance (as the wound covering device of the appliance would be oriented when placed on the body of a patient)
Figure 5B:
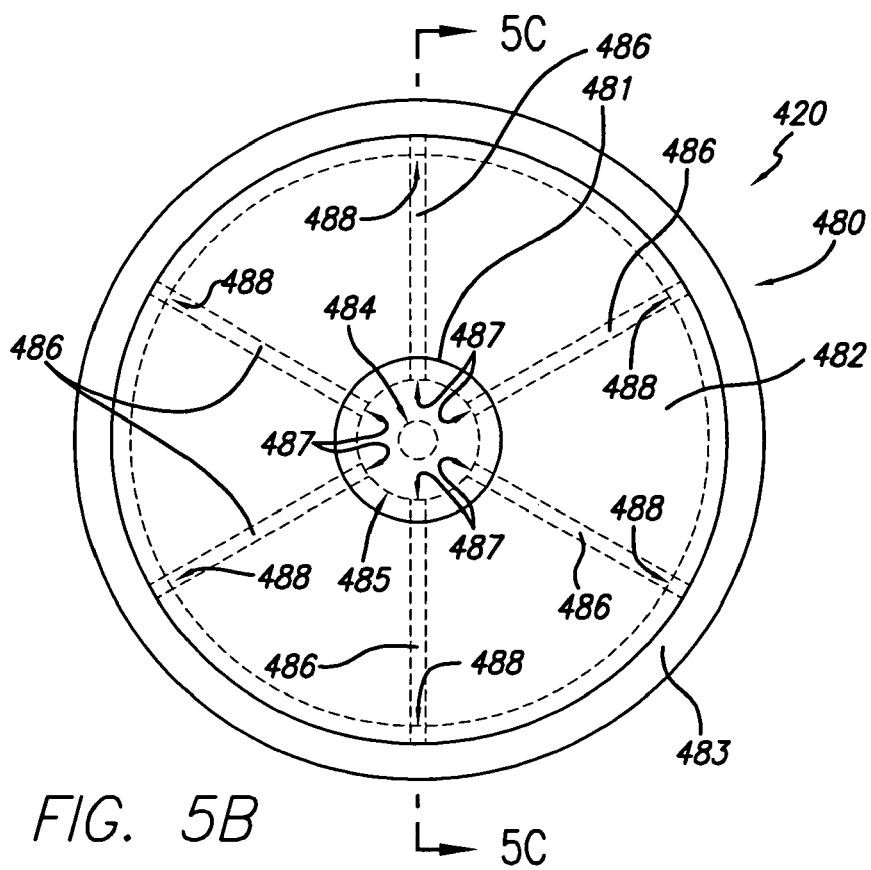
FIG. 5B is a plan view of the embodiment of the wound covering device of FIG. 5A from below the bottom end opening thereof, as taken along the lines 5B—5B of FIG. 5A.

An embodiment of a third version of the invention is illustrated in FIG. 5A, FIG. 5B, and FIG. 5C. In this embodiment, the appliance 410 is comprised of a wound covering device 420 and a vacuum system 450. The wound covering device 420 is further comprised of a fluid impermeable flexible overlay 480 and reduced pressure supply means, which are discussed in more detail below. In the illustrated embodiment, the impermeable overlay 480 is approximately bell-shaped, being comprised of an overlay top portion 481 and an overlay bottom portion 482, wherein the overlay bottom portion 482 is approximately cup-shaped, having a smaller opening at the other end 480a and a larger opening at one end 480b, the larger opening being the bottom end 480b opening of the impermeable overlay 480. In this embodiment, the overlay bottom portion 482 further comprises a flange portion 483 that is adjacent to and extends around the perimeter of the exterior portion of the bottom end 480b opening of the impermeable overlay 480. The flange portion 483 generally dissipates the force exerted by the perimeter of the bottom end 480b opening on the tissue 471 surrounding the wound 460 in the same manner as the embodiments of the flange portion 21f of the first version of the invention described above and illustrated in connection with FIG. 1A. In the embodiment illustrated in FIG. 5A, FIG. 5B, and FIG. 5C, the overlay top portion 481 is approximately cylindrical in shape, having an opening at each end 480a, 480c, one opening being a port end 480a of the impermeable overlay 480 and the other opening 480c being adjacent to the smaller opening 480c of the overlay bottom portion 482. In this embodiment, the port end 480a of the overlay top portion 481 has a port 484 therein that extends through the port end 480a to a chamber 485 that is positioned within the overlay top portion 481, so that the port 484 is in fluid communication with the chamber 485. Also in this embodiment, the impermeable overlay 480 is further comprised of at least one channel 486. The at least one channel 486 extends from an opening 487 in the chamber 485, so that the at least one channel 486 is in fluid communication with the chamber 485 (and thus, also the port 485) at the port end 480a, approximately parallel to the exterior surface of the impermeable overlay 480 to approximately the bottom open end 480b, where it terminates at an opening 488 in the interior surface of the impermeable overlay 480 so that the area of the wound 461 under the impermeable overlay 480 is in fluid communication with the port 484. In the illustrated embodiment, there are six channels 486. In other embodiments, there may be more or fewer channels. The preferred number of channels 486 generally depends upon the anticipated type of treatment of the wound 460, the size of the impermeable overlay 480, the anticipated amount of fluid to be aspirated from the wound 460, the level of reduced pressure required, and the individual preference of the user of the appliance 410. It is to be noted that the channels 486 may also be of almost any geometry and shape. For example, in other embodiments, the channels 486 may have a different cross-sectional shape or combination of shapes. Similarly, the channels 486 may follow a different path from the chamber 485 to the opening 488 near the bottom end 480b. For example, the channels 486 need not follow a symetric pattern, and may have more channels 486 on one side of the impermeable overlay 480 than on another side to increase flow in situations where the impermeable overlay 480 may not be level while in use. In still other embodiments, the channels 486 may be placed adjacent to the surface of the impermeable overlay 480, such as by tubes attached to the interior or exterior surface of the impermeable overlay 480. In yet other embodiments, the openings 488 may not all be the same distance from the bottom end 480b. For example, the openings 488 may be staggered so that some end approximately ¼ inch from the bottom end 480b, while others end approximately ½ inch from the bottom end 480b. In other embodiments, the openings 488 may be placed at almost any location on the interior surface of the impermeable overlay 480. The preferred shape, geometry and size of channels 486 generally depends upon the anticipated type of treatment of the wound, the size of the impermeable overlay 480, the anticipated amount of fluid to be aspirated from the wound 460, the level of reduced pressure required, and the individual preference of the user of the appliance 410. The port 484, the chamber 485, the channels 486, and the openings 487, 488 may be created in the impermeable overlay using any suitable manner currently known in the art or that may be developed in the art in the future, such as casting, injection molding, machining, and other means and combinations of such means. For example, as illustrated in FIG. 5C, the impermeable overlay may be fabricated in two parts—an outer section 482a and an inner section 482b. In this example, the features of the channels 486, the chamber 485, and the port 485 would be cast or machined into the outer section 482a. The inner section 482b would have the bottom openings 488 therein and would be adapted to be positioned adjacent to the inner surface of the outer section 482a. Thus, when the inner section 482b is attached (such as by an adhesive) to the outer section 482a, the features of the port 484, the chamber 485, the channels 486, and the openings 487, 488 would be created.

The bottom end 480b is positioned over the wound 460 on the tissue 471 surrounding the wound 460 so that it forms an approximately hermetic seal with such tissue 471 in substantially the same manner as the bottom end 21b of the impermeable overlay 21 of the first version of the invention is positioned over the wound 60 on the tissue 71 surrounding the wound 60, as described above and illustrated in connection with FIG. 1A. In addition, the impermeable overlay 480 is sufficiently rigid so that it is supported out of contact from the wound 460. In the various embodiments of this third version of the invention, the impermeable overlay 480 may have substantially the same structure, features characteristics and operation as the impermeable overlays 21, 121, 321 of the first version of the invention described above and illustrated in connection with FIG. 1A, FIG. 2, and FIG. 4, respectively, except that in this third version the at least one channel 486 is present in the impermeable overlay 480 and is in fluid communication with the port 485 and the chamber 485 in the port end 480a at one end of the at least one channel 486 and is in fluid communication with the interior surface openings 488 in the impermeable overlay 480 at the other end of the at least one channel 486. For example, in various embodiments of the third version of the invention, the impermeable overlay 480 may have any of the shapes provided in any of the embodiments of the impermeable overlays 21, 121, 321 of the first version of the invention described above and illustrated in connection with FIG. 1A, FIG. 2, and FIG. 4, respectively. It is to be noted that in other embodiments of this third version of the invention illustrated in FIG. 5A, FIG. 5B, and FIG. 5C, the overlay bottom portion 482 may be further comprised of a padding material placed between the perimeter of the bottom end 480b opening and the tissue surrounding the wound in the same manner that padding material may be included with the embodiments of the overlay bottom portion 21*d* of the first version of the invention described above and illustrated in connection with FIG. 1A. Further, in the embodiment illustrated in FIG. 5A, FIG. 5B, and FIG. 5C, the perimeter of the bottom end 480*b* opening of the impermeable overlay 480 may be approximately hermetically sealed to the tissue 471 surrounding the wound 460 using substantially the same tissue sealing means used to approximately hermetically seal the perimeter of the embodiments of the bottom end 21*b* opening of the impermeable overlay 21 of the first version of the invention to the tissue 71 surrounding the wound 60, as described above and illustrated in connection with FIG. 1A. The impermeable overlay 480 of the embodiment illustrated in FIG. 5A, FIG. 5B, and FIG. 5C may also be comprised of substantially the same materials and be constructed in the same manner as the embodiments of the impermeable overlay 21 of the first version of the invention described above and illustrated in connection with FIG. 1A.

In the embodiment of the third version of the invention illustrated in FIG. 5A, the vacuum system 450 is comprised of a reduced pressure supply source 430 and reduced pressure supply means 440, which is described in more detail below. In this embodiment, the reduced pressure supply source 430, which produces a source of reduced pressure or suction that is supplied to the wound covering device 420, includes a small, portable vacuum pump 431, a filter 433, and a power source (not illustrated) that is contained within the housing for the portable vacuum pump 34. In the illustrated embodiment, predetermined amounts of suction or reduced pressure are produced by the portable vacuum pump 431. The portable vacuum pump 431 is preferably controlled by a control device (not illustrated) that is also located within the housing for the portable vacuum pump 431, which may provide substantially the same functions as the control device 32 of the first version of the invention described above and illustrated in connection with FIG. 1A and FIG. 1B. Except for its smaller size, the portable vacuum pump 431 may operate in substantially the same manner as the vacuum pump 31 of the first version of the invention described above and illustrated in connection with FIG. 1A and FIG. 1B. In the embodiment illustrated in FIG. 5A, the filter 433 may have the same structure, features, characteristics and operation, and provide substantially the same functions, as the filter 33 of the first version of the invention described above and illustrated in connection with FIG. 1A and FIG. 1B. The power source may be any source of energy currently known in the art or that may be developed in the art in the future that may be used to power the portable vacuum pump 431. For example, in some embodiments, the power source may be a fuel cell or battery. In the illustrated embodiment, the filter 433 is rigidly connected to the portable vacuum pump 431. It is to be noted that in other embodiments of the third version of the invention, the reduced pressure supply source 430 may not have a filter 433.

In the embodiment of the third version of the invention illustrated in FIG. 5A, the reduced pressure supply means 440 of the vacuum system 450, which is used to connect the reduced pressure supply source 430 to the port 484 so that reduced pressure is supplied to the area of the wound under the impermeable overlay 480, is comprised of at least one tubing member 441. In this embodiment, the at least one tubing member 441 is a rigid tubing member. In other embodiments, the at least one tubing member may be sufficiently flexible to permit movement of the at least one tubing member 441, but is sufficiently rigid to resist constriction when reduced pressure is supplied to the port 484 or when the location of the wound is such that the patient must sit or lie upon the at least one tubing member 441 or upon the wound covering device 420. In the embodiment illustrated in FIG. 5A, the at least one tubing member 41 is connected to the port 484 by inserting one end of the at least one tubing member 441 into the port 484 and sealing (such as with an adhesive) the at least one tubing member 441 to the port 484. It is to be noted that in other embodiments of this third version of the invention, the at least one tubing member 441 may be connected to the port 484 using any suitable means currently known in the art or developed in the art in the future. Examples include the tubing connection means of the first and second versions of the invention discussed above and illustrated in connection with FIG. 1A, FIG. 1B, FIG. 2, FIG. 3, and FIG. 4. Similar means may be used to connect the other end of the at least one tubing member 441 to the reduced pressure supply source 430 providing the reduced pressure. In other embodiments of this third version of the invention, the reduced pressure supply means 440 may further comprises a fluid collection system (not illustrated), which may generally have the same structure, features, characteristics and operation, and perform the same functions, as the fluid collection system 42 of the first version of the invention described above and illustrated in connection with FIG. 1A and FIG. 1B.

In other embodiments of this third version of the invention, as illustrated in FIG. 5C, the vacuum system 450 may have substantially the same structure, features, characteristics and operation of the various embodiments of the vacuum system 50 of the first version of the invention described above and illustrated in connection with FIG. 1A and FIG. 1B and the vacuum system 190 and supplemental vacuum system 150 described above and illustrated in connection with FIG. 2. In addition, in the embodiment of the invention illustrated in FIG. 5C, the means used to connect the vacuum system 450 to the port 484 may be substantially the same as the means used to connect the vacuum system 50 to the top drain portion 23*b* and port 22 as described above and illustrated in connection with FIG. 1A and FIG. 1B, and the means used to connect the vacuum system 190 to the top drain portion 123*b*, as described above and illustrated in connection with FIG. 2.

The embodiments of this third version of the invention illustrated in FIG. 5A, FIG. 5B, and FIG. 5C may be operated using a variety of methods. One such method comprises the following steps. First, the bottom end 480*b* of the impermeable overlay 480 is operably placed over the wound 460 in a manner that an approximately hermetic seal is formed with the tissue 471 surrounding the wound 460 in the manner described above. Second, the at least one tubing member 441 is operably connected to the reduced pressure supply source 450 using the reduced pressure supply means 440. It should be noted that the preceding steps may generally be performed in any order. Third, the reduced pressure supply source 450 is operated in a manner so that it provides a supply of reduced pressure to maintain reduced pressure in the area of the wound 461 under the impermeable overlay 480. Fourth, reduced pressure is maintained in the area of the wound 461 under the impermeable overlay 480 until the wound 461 being treated has progressed toward a selected stage of healing. In other embodiments, the reduced pressure is from about 20 mm of Hg below atmospheric pressure to about 125 mm of Hg below atmospheric pressure. In other embodiments, the reduced pressure is applied in a cyclic nature, the cyclic nature providing alternating time periods of application of reduced pressure and without application of reduced pressure. In some of these embodiments, the pressure may be applied for a period of approximately 6 to 8 hours during a period each day when the patient is sleeping.

What is claimed is:

1. An appliance for administering reduced pressure treatment to a wound, the appliance comprising:
   (a) an impermeable overlay comprised of a top end having an opening therein and a bottom end having an opening therein, wherein:
      (i) the bottom end is positioned over the wound on the tissue surrounding the wound so that the impermeable overlay encloses the wound and forms an approximately hermetic seal with such tissue; and
      (ii) the impermeable overlay is sufficiently rigid so that it supports a stopper and is supported out of contact with the wound;
   (b) a stopper having a port therein, the stopper being removably positioned in the top end opening of the impermeable overlay and forming an approximately hermetic seal with the top end opening of the impermeable overlay;
   (c) a suction drain comprised of a top drain portion positioned within the port in the stopper and a bottom drain portion extending from the top drain portion into the area of the wound under the impermeable overlay;
   (d) suction drain sealing means to seal the top drain portion to the port in the stopper; and
   (e) reduced pressure supply means to connect the top portion of the suction drain to a reduced pressure supply source that provides a supply of reduced pressure to the suction drain, so that the area under the impermeable overlay in the area of the wound is supplied with reduced pressure by the reduced pressure supply source.

2. The appliance of claim 1, wherein the impermeable overlay is essentially bell-shaped, the bottom end opening of the impermeable overlay having a larger diameter than the top end opening of the impermeable overlay.

3. The appliance of claim 1, wherein the impermeable overlay is comprised of an overlay top portion and an overlay bottom portion, wherein:
   (a) the overlay bottom portion is essentially conical in shape, having a larger opening at one end and a smaller opening at the other end, the larger opening being the bottom end opening of the impermeable overlay; and
   (b) the overlay top portion is essentially in the shape of a cylindrical tube having an opening at each end, one opening being the top end opening of the impermeable overlay and the other opening being adjacent to the smaller opening of the overlay bottom portion.

4. The appliance of claim 3, wherein the overlay bottom portion further comprises a flange portion that is adjacent to and extends around the perimeter of the exterior portion of the bottom open end of the impermeable overlay.

5. The appliance of claim 1, wherein the impermeable overlay is comprised of:
   (a) an essentially conically-shaped semi-rigid flange portion adjacent to the perimeter of the bottom end opening;
   (b) an essentially conically-shaped flexible center portion that extends away from the semi-rigid flange portion;
   (c) a cylindrical tubular overlay top portion extending away from the flexible center portion, wherein the distal open end of the overlay top portion is the top end opening of the impermeable overlay and the overlay top portion is sufficiently rigid to hold and support the stopper; and
   (d) at least two support members that are each connected at one end to the semi-rigid flange portion and at the other end to the overlay top portion, wherein the at least two support members are sufficiently rigid to support the overlay top end out of contact with the semi-rigid flange portion.

6. The appliance of claim 1, wherein:
   (a) the top end opening of the impermeable overlay is approximately in the shape of a circle;
   (b) the stopper is essentially in the shape of a cylinder being tapered along its longitudinal axis so that one base of the cylinder has a smaller diameter than the other base; and
   (c) the smaller diameter base of the stopper is within the volume of the impermeable overlay and the larger diameter base of the stopper is outside the volume of the impermeable overlay when the stopper is removably positioned in the top end opening of the impermeable overlay.

7. The appliance of claim 1, wherein the port in the stopper is approximately cylindrical in shape and the suction drain is essentially tubular in shape, wherein the top drain portion of the tubular suction drain is positioned within the port.

8. The appliance of claim 7, wherein the top drain portion is comprised of flexible tubing and the bottom drain portion of the suction drain is comprised of flexible tubing and wound suction means that may be used to remove debris, exudate and other matter from the wound.

9. The appliance of claim 8, wherein the wound suction means is comprised of:
   (a) a wound suction member having an essentially rectangular cross section, a hollow interior, and at least one perforation in the surface of the wound suction member; and
   (b) wound suction member attachment means to connect the wound suction member to the bottom drain portion;
   (c) wherein the bottom drain portion is in fluid communication with the wound suction member.

10. The appliance of claim 7, wherein the top drain portion of the suction drain is further comprised of tubing connection means that are used to removably connect the reduced pressure supply means to the top drain portion of the suction drain.

11. The appliance of claim 1, further comprising a reduced pressure supply source, wherein the reduced pressure supply source at least produces a supply of reduced pressure and is connected to the top drain portion of the suction drain by the reduced pressure supply means, so that the area under the impermeable overlay in the area of the wound is supplied with reduced pressure by the reduced pressure supply source.

12. The appliance of claim 11, wherein the reduced pressure supply source is comprised of:
   (a) a suction bulb having an inlet port and an outlet port, wherein the inlet port is operably connected to the reduced pressure supply means and fluids generally exit the suction bulb by means of the outlet port;
   (b) an exhaust tubing member operably connected to the outlet port; and
   (c) an exhaust control valve operably connected to the exhaust tubing member.

13. The appliance of claim 12, wherein the reduced pressure supply source is further comprised of a filter operably connected to the exhaust tubing member, wherein the filter prevents the venting of micro-organisms aspirated from the wound or fluids aspirated from the wound, or both.

14. The appliance of claim 11, wherein the reduced pressure supply source is comprised of a vacuum pump.

15. The appliance of claim 14, wherein the reduced pressure supply source further comprises a control system for the vacuum source, wherein the control system controls at least the level of suction produced by the vacuum pump or the rate of fluid flow produced by the vacuum pump or any combination of rate of suction and rate of fluid flow of the vacuum pump.

16. The appliance of claim 14, wherein the reduced pressure supply source further comprises a filter operably positioned between the vacuum pump and the reduced pressure supply means, wherein the filter prevents the venting of and contamination of the vacuum pump by microorganisms aspirated from the wound or fluids aspirated from the wound, or both.

17. The appliance of claim 14, wherein the vacuum pump is a portable vacuum pump.

18. A method of using the appliance of claim 11 to treat a wound, such method comprising the steps of:
   (a) operably positioning the suction drain in the port in the stopper;
   (b) operably positioning the stopper in the top end opening of the impermeable overlay;
   (c) operably placing the bottom end of the impermeable overlay over the wound;
   (d) operably connecting the suction drain to the reduced pressure supply source using the reduced pressure supply means;
   (e) operating the reduced pressure supply source, wherein the reduced pressure supply source provides a supply of reduced pressure to maintain reduced pressure in the area of the wound under the impermeable overlay; and
   (f) maintaining the reduced pressure in the area of the wound under the impermeable overlay until the wound being treated has progressed toward a selected stage of healing.

19. The method of claim 18, further comprising the step of removing the stopper from the top end opening of the impermeable overlay to provide access for treatment of the wound.

20. The method of claim 18, further comprising the step of manipulating the suction drain so that the suction drain removes debris, fluid and other material from the area of the wound under the impermeable overlay.

21. The method of claim 18, wherein the reduced pressure is from about 20 mm of Hg below atmospheric pressure to about 125 mm of Hg below atmospheric pressure.

22. The method of claim 18, wherein the reduced pressure is applied in a cyclic nature, the cyclic nature providing alternating time periods of application of reduced pressure and without application of reduced pressure.

23. The appliance of claim 1, wherein the reduced pressure supply means is comprised of flexible tubing.

24. The appliance of claim 1, wherein the reduced pressure supply means is comprised of a collection system that is operably positioned between the stopper and the reduced pressure supply source and the collection system comprises a container to receive and hold fluid aspirated from the wound.

25. The appliance of claim 24, wherein the reduced pressure supply means is further comprised of flexible tubing that connects the collection system to the suction drain and the collection system to the reduced pressure supply source.

26. The appliance of claim 24, wherein the collection system is further comprised of pressure halting means to halt the application of reduced pressure to the wound when the fluid in the container exceeds a predetermined amount.

27. The appliance of claim 26, wherein the reduced pressure supply means is further comprised of a tubing member that is connected to the collection system and the pressure halting means is comprised of a flotation valve within the container for blocking the flexible tubing member when a predetermined amount of fluid is collected within the container.

28. The appliance of claim 1, wherein the reduced pressure under the impermeable overlay in the area of the wound is in the range from approximately 20 mm of Hg below atmospheric pressure to approximately 125 mm of Hg below atmospheric pressure.

29. The appliance of claim 1, wherein the reduced pressure is applied in a cyclic nature, the cyclic nature providing alternating time periods of application of reduced pressure and without application of reduced pressure.

30. An appliance for administering reduced pressure treatment to a wound, the appliance comprising:
   (a) a wound covering device, which is further comprised of:
      (i) an impermeable overlay comprised of a top end having an opening therein and a bottom end having an opening therein, wherein the bottom end is positioned over the wound on the tissue surrounding the wound so that the impermeable overlay encloses the wound and the impermeable overlay is sufficiently rigid to be supported out of contact with the wound;
      (ii) tissue sealing means to seal the impermeable overlay to tissue surrounding the wound so that the impermeable overlay is adapted to maintain reduced pressure under the wound covering device in the area of the wound;
      (iii) a stopper having a port therein, the stopper being removably positioned in the top end opening of the impermeable overlay and forming an approximately hermetic seal with the top end opening of the impermeable overlay;
      (iv) a suction drain comprised of a top drain portion positioned within the port in the stopper and a bottom drain portion extending from the top drain portion into the area of the wound under the impermeable overlay; and
      (v) suction drain sealing means to seal the top drain portion to the port in the stopper; and
   (b) a vacuum system comprised of:
      (i) a reduced pressure supply source, comprised from the group consisting of a suction bulb, a vacuum pump, a portable vacuum pump, or any combination thereof, for providing a supply of reduced pressure;
      (ii) reduced pressure supply means to connect the reduced pressure supply source to the wound covering device, so that the area under the wound covering device in the area of the wound is supplied with reduced pressure by the vacuum pump; and
      (iii) a collection system that is operably positioned within the reduced pressure supply means between the wound covering device and the reduced pressure supply source, the collection system comprising a container to receive and hold fluid aspirated from the wound.

31. The appliance of claim 30, wherein the impermeable overlay is essentially bell-shaped, wherein the bottom end opening of the impermeable overlay has a larger diameter than the top end opening of the impermeable overlay.

32. The appliance of claim 30, wherein the impermeable overlay is comprised of an overlay top portion and an overlay bottom portion, wherein:
(a) the overlay bottom portion is essentially conical in shape, having a larger opening at one end and a smaller opening at the other end, the larger opening being the bottom end opening of the impermeable overlay; and
(b) the overlay top portion is essentially in the shape of a cylindrical tube having an opening at each end, one opening being the top end opening of the impermeable overlay and the other opening being adjacent to the smaller opening of the overlay bottom portion.

33. The appliance of claim 32, wherein the overlay bottom portion further comprises a flange portion that is adjacent to and extends around the perimeter of the exterior portion of the bottom open end of the impermeable overlay.

34. The appliance of claim 33, wherein:
(a) the top end opening of the impermeable overlay is essentially in the shape of a circle;
(b) the stopper is essentially in the shape of a cylinder being tapered along its longitudinal axis so that one base of the cylinder has a smaller diameter than the other base; and
(c) the smaller diameter base of the stopper is within the volume of the impermeable overlay and the larger diameter base of the stopper is outside the volume of the impermeable overlay when the stopper is removably positioned in the top end opening of the impermeable overlay.

35. The appliance of claim 34, wherein:
(a) the port in the stopper is essentially cylindrical in shape;
(b) the top drain portion and the bottom drain portion of the suction drain are comprised of flexible tubing; and
(c) the bottom drain portion of the suction drain is further comprised of:
(i) a wound suction member; and
(ii) wound suction member attachment means to connect the wound suction member to the bottom drain portion, wherein the bottom drain portion is in fluid communication with the wound suction member.

36. The appliance of claim 30, wherein the impermeable overlay is comprised of:
(a) an essentially conically-shaped semi-rigid flange portion adjacent to the perimeter of the bottom end opening;
(b) an essentially conically-shaped flexible center portion that extends away from the semi-rigid flange portion;
(c) a cylindrical tubular overlay top portion extending away from the flexible center portion, wherein the distal open end of the overlay top portion is the top end opening of the impermeable overlay and the overlay top portion is sufficiently rigid to hold and support the stopper; and
(d) at least two support members that are each connected at one end to the semi-rigid flange portion and at the other end to the overlay top portion, the at least two support members being sufficiently rigid to support the overlay top end out of contact with the semi-rigid flange portion.

37. The appliance of claim 30, wherein the tissue sealing means is the reduced pressure maintained under the wound covering device.

38. The appliance of claim 30, wherein the tissue sealing means is an adhesive tape.

39. The appliance of claim 30, wherein the tissue sealing means is a stretch fabric that covers the impermeable overlay and the stopper, wherein the stretch fabric is wrapped around a portion of the body of the patient in the area of the wound.

40. An appliance for administering reduced pressure treatment to a wound, the appliance comprising:
(a) an impermeable overlay comprised of a port end having a port and a bottom end having an opening therein, wherein:
(i) the bottom end is positioned over the wound on the tissue surrounding the wound so that the impermeable overlay encloses the wound and forms an approximately hermetic seal with such tissue; and
(ii) the impermeable overlay is sufficiently rigid so that it is supported out of contact from the wound;
(b) a suction drain comprised of a top drain portion positioned within the port and a bottom drain portion extending from the top drain portion into the area of the wound under the impermeable overlay;
(c) suction drain sealing means to seal the top drain portion to the port; and
(d) reduced pressure supply means to connect the top portion of the suction drain to a reduced pressure supply source that provides a supply of reduced pressure to the suction drain, so that the area under the impermeable overlay in the area of the wound is supplied with reduced pressure by the reduced pressure supply source.

41. The appliance of claim 40, wherein the impermeable overlay is essentially bell-shaped, wherein the bottom end opening of the impermeable overlay has a larger diameter than the top end opening of the impermeable overlay.

42. The appliance of claim 40, wherein the impermeable overlay is comprised of an overlay top portion and an overlay bottom portion, wherein:
(a) the overlay bottom portion is essentially conical in shape, having a larger opening at one end and a smaller opening at the other end, the larger opening being the bottom end opening of the impermeable overlay; and
(b) the overlay top portion is essentially in the shape of a cylindrical tube being open at one end and closed at the other end, wherein the closed end has a port therein that is the port in the port end of the impermeable overlay and the open end is adjacent to the smaller opening of the overlay bottom portion.

43. The appliance of claim 42, wherein the overlay bottom portion further comprises a flange portion that is adjacent to and extends around the perimeter of the exterior portion of the bottom open end of the impermeable overlay.

44. The appliance of claim 40, wherein the impermeable overlay is comprised of:
(a) an essentially conically-shaped semi-rigid flange portion adjacent to the perimeter of the bottom end opening;
(b) an essentially conically-shaped flexible center portion that extends away from the semi-rigid flange portion;
(c) a cylindrical tubular overlay top portion extending away from the flexible center portion, the overlay top portion being open at one end and closed at the other end, wherein the open end is adjacent to the flexible center portion and the closed end has a port therein that is the port in the port end of the impermeable overlay; and
(d) at least two support members that are each connected at one end to the semi-rigid flange portion and at the other end to the overlay top portion, the at least two support members being sufficiently rigid to support the overlay top end out of contact with the semi-rigid flange portion.

45. The appliance of claim 40, wherein the port is approximately cylindrical in shape and the suction drain is essentially tubular in shape, wherein the top drain portion of the tubular suction drain is positioned within the port.

46. The appliance of claim 45, wherein the top drain portion is comprised of flexible tubing and the bottom drain portion of the suction drain is comprised of flexible tubing and wound suction means that may be used to remove debris, exudate and other matter from the wound.

47. The appliance of claim 46, wherein the wound suction means is comprised of:
    (a) a wound suction member having an approximately rectangular cross section, a hollow interior, and at least one perforation in the surface of the wound suction member; and
    (b) wound suction member attachment means to connect the wound suction member to the bottom drain portion;
    (c) wherein the bottom drain portion is in fluid communication with the wound suction member.

48. The appliance of claim 40, further comprising a reduced pressure supply source, wherein the reduced pressure supply source at least produces a supply of reduced pressure and is connected to the top drain portion of the suction drain by the reduced pressure supply means, so that the area under the impermeable overlay in the area of the wound is supplied with reduced pressure by the reduced pressure supply source.

49. The appliance of claim 48, wherein the reduced pressure supply source is comprised of:
    (a) a suction bulb having an inlet port and an outlet port, wherein the inlet port is operably connected to the reduced pressure supply means and fluids generally exit the suction bulb by means of the outlet port;
    (b) an exhaust tubing member operably connected to the outlet port;
    (c) an exhaust control valve operably connected to the exhaust tubing member; and
    (d) a filter operably connected to the exhaust tubing member, wherein the filter prevents the venting of micro-organisms aspirated from the wound or fluids aspirated from the wound, or both.

50. The appliance of claim 48, wherein the reduced pressure supply source is comprised of a vacuum pump.

51. The appliance of claim 50, wherein the reduced pressure supply source further comprises a control system for the vacuum source, wherein the control system controls at least the level of suction produced by the vacuum pump or the rate of fluid flow produced by the vacuum pump or any combination of rate of suction and rate of fluid flow of the vacuum pump.

52. The appliance of claim 50, wherein the reduced pressure supply source further comprises a filter operably positioned between the vacuum pump and the reduced pressure supply means, wherein the filter prevents the venting of and contamination of the vacuum pump by micro-organisms aspirated from the wound or fluids aspirated from the wound, or both.

53. The appliance of claim 50, wherein the vacuum pump is a portable vacuum pump.

54. A method of using the appliance of claim 48 to treat a wound, such method comprising the steps of:
    (a) operably positioning the suction drain in the port of the port end of the impermeable overlay;
    (b) operably placing the bottom end of the impermeable overlay over the wound;
    (c) operably connecting the suction drain to the reduced pressure supply source using the reduced pressure supply means;
    (d) operating the reduced pressure supply source, wherein the reduced pressure supply source provides a supply of reduced pressure to maintain reduced pressure in the area of the wound under the impermeable overlay; and
    (e) maintaining the reduced pressure in the area of the wound under the impermeable overlay until the wound being treated has progressed toward a selected stage of healing.

55. The method of claim 54, further comprising the step of manipulating the suction drain so that the suction drain removes debris, fluid and other material from the area of the wound under the impermeable overlay.

56. The method of claim 54, wherein the reduced pressure is from about 20 mm of Hg below atmospheric pressure to about 125 mm of Hg below atmospheric pressure.

57. The method of claim 54, wherein the reduced pressure is applied in a cyclic nature, the cyclic nature providing alternating time periods of application of reduced pressure and without application of reduced pressure.

58. The appliance of claim 40, wherein the reduced pressure supply means is comprised of flexible tubing.

59. The appliance of claim 40, wherein the reduced pressure supply means is comprised of a collection system that is operably positioned between the stopper and the reduced pressure supply source and the collection system comprises a container to receive and hold fluid aspirated from the wound.

60. The appliance of claim 59, wherein the reduced pressure supply means is further comprised of flexible tubing that connects the collection system to the suction drain and the reduced pressure supply source.

61. The appliance of claim 59, wherein the collection system is further comprised of pressure halting means to halt the application of reduced pressure to the wound when the fluid in the container exceeds a predetermined amount.

62. An appliance for administering reduced pressure treatment to a wound, the appliance comprising:
    (a) an impermeable overlay comprised of a port end having a port and a bottom end having an opening therein, wherein:
        (i) the bottom end is positioned over the wound on the tissue surrounding the wound so that the impermeable overlay encloses the wound and forms an approximately hermetic seal with such tissue;
        (ii) the impermeable overlay is sufficiently rigid so that it is supported out of contact with the wound; and
        (iii) the impermeable overlay is further comprised of at least one channel in fluid communication with the port at the port end, the at least one channel extending from the port approximately parallel to a surface of the impermeable overlay to a point between the port and the bottom end opening, the at least one channel terminating at an opening in the interior surface of the impermeable overlay so that the area of the wound under the impermeable overlay is in fluid communication with the port; and
    (b) reduced pressure supply means to connect the port of the port end to a reduced pressure supply source that provides a supply of reduced pressure to the port, so that the area under the impermeable overlay in the area of the wound is supplied with reduced pressure by the reduced pressure supply source.

63. The appliance of claim 62, wherein the impermeable overlay is essentially bell-shaped, wherein the bottom end opening of the impermeable overlay has a larger diameter than the top end opening of the impermeable overlay.

64. The appliance of claim 62, wherein the impermeable overlay is comprised of an overlay top portion and an overlay bottom portion, wherein:
 (a) the overlay bottom portion is essentially conical in shape, having a larger opening at one end and a smaller opening at the other end, the larger opening being the bottom end opening of the impermeable overlay; and
 (b) the overlay top portion is essentially in the shape of a cylindrical tube being open at one end and closed at the other end, wherein the closed end has a port therein that comprises the port in the port end of the impermeable overlay and the open end is adjacent to the smaller opening of the overlay bottom portion.

65. The appliance of claim 64, wherein the overlay bottom portion further comprises a flange portion that is adjacent to and extends around the perimeter of the exterior portion of the bottom open end of the impermeable overlay.

66. The appliance of claim 62, wherein the at least one channel extends to within at least ¼ inch of the bottom end opening of the impermeable overlay.

67. The appliance of claim 62, wherein there are at least two channels and the at least two channels terminate at openings that are different distances from the bottom end opening of the impermeable overlay.

68. The appliance of claim 62, wherein there are four channels.

69. The appliance of claim 62, further comprising a reduced pressure supply source, wherein the reduced pressure supply source at least produces a supply of reduced pressure and is connected to the top drain portion of the suction drain by the reduced pressure supply means, so that the area under the impermeable overlay in the area of the wound is supplied with reduced pressure by the reduced pressure supply source.

70. The appliance of claim 69, wherein the reduced pressure supply source is comprised of:
 (a) a suction bulb having an inlet port and an outlet port, wherein the inlet port is operably connected to the reduced pressure supply means and fluids generally exit the suction bulb by means of the outlet port;
 (b) an exhaust tubing member operably connected to the outlet port;
 (c) an exhaust control valve operably connected to the exhaust tubing member; and
 (d) a filter operably connected to the exhaust tubing member, wherein the filter prevents the venting of micro-organisms aspirated from the wound or fluids aspirated from the wound or both.

71. The appliance of claim 69, wherein the reduced pressure supply source is comprised of a vacuum pump.

72. The appliance of claim 71, wherein the reduced pressure supply source further comprises a control system for the vacuum source, wherein the control system controls at least the level of suction produced by the vacuum pump or the rate of fluid flow produced by the vacuum pump or any combination of rate of suction and rate of fluid flow of the vacuum pump.

73. The appliance of claim 71, wherein the reduced pressure supply source further comprises a filter operably positioned between the vacuum pump and the reduced pressure supply means, wherein the filter prevents the venting of and contamination of the vacuum pump by micro-organisms aspirated from the wound or fluids aspirated from the wound or both.

74. The appliance of claim 71, wherein the vacuum pump is a portable vacuum pump.

75. A method of using the appliance of claim 69 to treat a wound, such method comprising the steps of:
 (a) operably placing the bottom end of the impermeable overlay over the wound;
 (b) operably connecting the port in the port end to the reduced pressure supply source using the reduced pressure supply means;
 (c) operating the reduced pressure supply source, wherein the reduced pressure supply source provides a supply of reduced pressure to maintain reduced pressure in the area of the wound under the impermeable overlay; and
 (d) maintaining the reduced pressure in the area of the wound under the impermeable overlay until the wound being treated has progressed toward a selected stage of healing.

76. The method of claim 75, wherein the reduced pressure is from about 20 mm of Hg below atmospheric pressure to about 125 mm of Hg below atmospheric pressure.

77. The method of claim 75, wherein the reduced pressure is applied in a cyclic nature, the cyclic nature providing alternating time periods of application of reduced pressure and without application of reduced pressure.

78. The appliance of claim 62, wherein the reduced pressure supply means is comprised of flexible tubing.

79. The appliance of claim 62, wherein the reduced pressure supply means is comprised of a collection system that is operably positioned between the port and the reduced pressure supply source and the collection system comprises a container to receive and hold fluid aspirated from the wound.

80. The appliance of claim 79, wherein the reduced pressure supply means is further comprised of flexible tubing that connects the collection system to the port and the reduced pressure supply source.

81. The appliance of claim 79, wherein the collection system is further comprised of pressure halting means to halt the application of reduced pressure to the wound when the fluid in the container exceeds a predetermined amount.

82. An appliance for administering reduced pressure treatment to a wound, the appliance comprising:
 (a) an impermeable overlay having a port and an opening, wherein:
  (i) the impermeable overlay is of a size and shape adapted to cover the wound;
  (ii) the portion of the impermeable overlay adjacent to the perimeter of the opening of the impermeable overlay is placed adjacent to the tissue surrounding the wound so that the impermeable overlay encloses the wound and forms an approximately hermetic seal with such tissue; and
  (iii) the impermeable overlay is sufficiently rigid so that it is supported out of contact from the wound;
 (b) a suction drain comprised of a top drain portion positioned within the port and a bottom drain portion extending from the top drain portion into the area of the wound under the impermeable overlay;
 (c) suction drain sealing means to seal the top drain portion to the port; and
 (d) reduced pressure supply means to connect the top portion of the suction drain to a reduced pressure supply source that provides a supply of reduced pressure to the suction drain, so that the area under the impermeable overlay in the area of the wound is supplied with reduced pressure by the reduced pressure supply source.

* * * * *